United States Patent [19]

Inoue et al.

[11] Patent Number: 5,510,244
[45] Date of Patent: Apr. 23, 1996

[54] APPARATUS AND METHOD FOR ASSAYING OPTICAL ISOMERS

[75] Inventors: Yukie Inoue, Tsuzuki; Ryuzo Hayashi, Higashiosaka; Naoka Matsuya, Sakai, all of Japan

[73] Assignee: Kanzaki Paper Manufacturing Co., Ltd., Tokyo, Japan

[21] Appl. No.: 67,960

[22] Filed: May 27, 1993

[30] Foreign Application Priority Data

| | | | |
|---|---|---|---|
| May 29, 1992 | [JP] | Japan | 4-139491 |
| Aug. 31, 1992 | [JP] | Japan | 4-232018 |
| Oct. 30, 1992 | [JP] | Japan | 4-293015 |
| Dec. 7, 1992 | [JP] | Japan | 4-327057 |

[51] Int. Cl.$^6$ .............................. C12Q 1/32; G01N 21/00
[52] U.S. Cl. .................. 435/26; 435/4; 435/28; 435/39; 435/139; 435/174; 435/175; 435/810; 435/973; 435/975; 435/286.1; 435/287.1; 435/286.5; 422/61; 422/68.1; 422/82; 422/82.01; 422/82.05; 422/102
[58] Field of Search ..................... 435/26, 4, 28, 435/39, 139, 174, 175, 287, 288, 291, 294, 810, 973, 975; 422/61, 68.1, 82, 82.01, 82.05, 102

[56] References Cited

FOREIGN PATENT DOCUMENTS

| | | | |
|---|---|---|---|
| 0310824 | 4/1989 | European Pat. Off. | C12M 1/40 |
| 2042722 | 6/1979 | United Kingdom | C12Q 1/26 |

OTHER PUBLICATIONS

Yao et al, *Chemical Abstract*, vol. 110, p. 714, Ref. No. 241864e, 1989 (Chem. Express 3(9), 559–62, 1988).

Okada et al, *Agric. Biol. Chem.*, vol. 42, No. 9, pp. 1781–1783, 1978.

Buttery et al, *Clin. Biochem.* vol. 20, pp. 237–239, Aug. 1987.

Tunail et al, *Chemical Abstracts*, vol. 110, p. 318, Ref. No. 91050v, 1988.

Kern et al, *Agric. Biol. Chem.* vol. 42, No. 6, pp. 1275–1278, 1978.

Buttery et al, *Colorimetric measurement of D(—) lactate in plasma*, Aug. 1987, Clin Biochem, vol. 20, No. 4, pp. 237–239 (only medline Abstract No.: 88080940 is provided).

*Primary Examiner*—Christina Y. Chan
*Assistant Examiner*—Abdel A. Mohamed
*Attorney, Agent, or Firm*—Larson and Taylor

[57] ABSTRACT

A method, apparatus and kit for assaying the L- and D-optical isomers and optionally the oxidation product derived from a L- (or D-) optical isomer.

20 Claims, 3 Drawing Sheets

APPARATUS AND METHOD FOR ASSAYING OPTICAL ISOMERS

TECHNICAL FIELD

The present invention relates to an apparatus and method for assaying optical isomers rapidly and in a simple and easy manner by utilizing an enzymatic reaction.

PRIOR ART

Among oxidation products derived from optical isomers, pyruvic acid, for instance, is an intermediate metabolite in the glycolysis and a starting material convertible to various organic acids such as lactic acid, malic acid and oxalacetic acid. Pyruvic acid plays an important role not only in glycolysis but also in amino acid metabolism, fatty acid metabolism and the like. Therefore, it is of great value to determine pyruvic acid levels in blood and other body fluids or to assay pyruvic acid as a substrate or product in determining the activity of a certain enzyme in a certain metabolic system. Furthermore, abnormal fermentation in such fermentation processes as alcohol fermentation and lactic acid fermentation processes leads to the formation of pyruvic acid.

As regards optical isomers like lactic acid, on the other hand, lactic acid fermentation has found wide application in food industry. Thus, for example, lactic acid fermentation using microorganisms has been used in the production of not only lactic acid and lactic drinks but also cheese, butter, sake, soy sauce, miso, pickles and the like. Among microorganisms used in such lactic acid fermentation, there are lactic acid bacteria and fungi, i.e., mould. Among them, lactic acid bacteria include species producing D-lactic acid alone, species producing L-lactic acid alone and species producing a mixture of D-lactic acid and L-lactic acid, as well known in the art.

Assaying of D-lactic acid and L-lactic acid in the fermentation process is therefore essential for fermentation process control and contamination detection, among others.

In the prior art, D-lactic acid is assayed by using D-lactate dehydrogenase (hereinafter briefly referred to as "D-LDH") and the oxidized-form coenzyme nicotinamide adenine dinucleotide (hereinafter briefly referred to as "NAD") and assaying the product formed, namely reduced-form nicotinamide adenine dinucleotide (hereinafter briefly referred to as "NADH") or pyruvic acid, by absorptiometry or fluorometry. However, this assay method has various problems caused by certain properties of D-LDH.

First, the reaction efficiency is low and therefore, at practical levels, the enzyme amount required is too large; this raises the cost of analysis. For reducing the enzyme amount, such measures as prolongation of the reaction time and adjustment of the reaction temperature are conceivable. However, these measures have negative effects: the procedure becomes complicated and troublesome and the assay time becomes longer. Secondly, the equilibrium of the reaction in which D-LDH is involved is favorable for the formation of D-lactic acid from NADH and pyruvic acid and therefore the reaction stops before conversion of the whole amount of D-lactic acid to pyruvic acid. For complete conversion of D-lactic acid to pyruvic acid, new means, for example consumption of the produced pyruvic acid by means of glutamic-pyruvic transaminase, is necessary, making the reaction process complicated and raising the cost of analysis.

For assaying not only D-lactic acid but also L-lactic acid, it is necessary to first assay one of them, for example D-lactic acid, and then perform the same assay procedure as for D-lactic acid using L-lactate dehydrogenase (hereinafter briefly referred to as "L-LDH"). This makes the assay procedure complicated and doubles the assay time and cost.

Furthermore, the assay method using lactate dehydrogenase is apt to undergo the influence of turbidity and coloring matter in the sample since the general method of detecting the enzymatic reaction is based on the change in the absorbance of NAD or NADH in the ultraviolet region as caused by the reaction.

In assaying such optical isomers as amino acids, it is difficult to perform exact assays for the D-form or L-form in a short time.

For assaying pyruvic acid, the above-mentioned method using L-LDH and NADH and a method using pyruvate oxidase are available, among others. In contrast to the assay of L-lactic acid, the method using L-LDH and NADH determines the decrease in the amount of NADH by means of absorptiometry. For determining both the D- and L-lactic acid and pyruvic acid levels, however, lactic acid assay must be performed by some other method.

As another method of assaying pyruvic acid, there may be mentioned the method using the reaction involving pyruvate oxidase. This method requires the use of thiamine pyrophosphate and flavine adenine dinucleotide as coenzymes, and bivalent ions such as magnesium, calcium, cobalt, manganese, etc., as activating factors, and causes formation of acetyl-phosphate, carbon dioxide and hydrogen peroxide from inorganic phosphate and oxygen. However, this enzymatic method is impracticable since the enzyme is rather unstable and expensive coenzymes are required in large amounts.

Among the methods of assaying L-lactic acid, there is a method which uses L-lactate oxidase (hereinafter briefly referred to as "LOD"). This method causes formation of hydrogen peroxide and pyruvic acid from L-lactic acid and oxygen. This reaction does not require any coenzyme. L-Lactic acid can be assayed by determining the amount of hydrogen peroxide formed in said reaction using a spectrophotometer. However, the colorimetric method has the problems mentioned above.

In view of the foregoing, the so-far disclosed methods of assaying the D- and L-optical isomers, for example the two components D-lactic acid and L-lactic acid, or of assaying three components, namely the D-isomer and L-isomer and the oxidation product derived from said isomer, for example D-lactic acid, L-lactic acid and pyruvic acid, can hardly be said to be satisfactorily practicable.

It is an object of the present invention to assay the two components, namely the D- and L-optical isomers exactly and precisely in a short time and in a simple and easy manner using a D-dehydrogenase (D-DH) and a L-dehydrogenase (L-DH).

It is another object of the invention to provide an assay apparatus and an assay method for assaying said two components, namely the L- and D-optical isomers exactly and precisely in a short time and in a simple and easy manner using the L-DH and D-DH each in an immobilized form.

It is a further object of the invention to provide a kit for assaying the D- and L-optical isomers and the oxidation product derived from the isomer exactly and precisely in a short time and in a simple and easy manner.

When a sufficient time is spent for the conversion reaction of the L-isomer and D-isomer, the sample becomes a mixture of both in a ratio of approximately 1:1 and the working curves 2 and 3 mentioned below under 12 are almost in agreement with each other, hence calculation can be made using two working curves, namely working curve 1 and working curve 2 or 3. It is to be understood that what is mentioned under 12 is a generalization including this and other cases.

SUMMARY OF THE INVENTION

Figure 1:
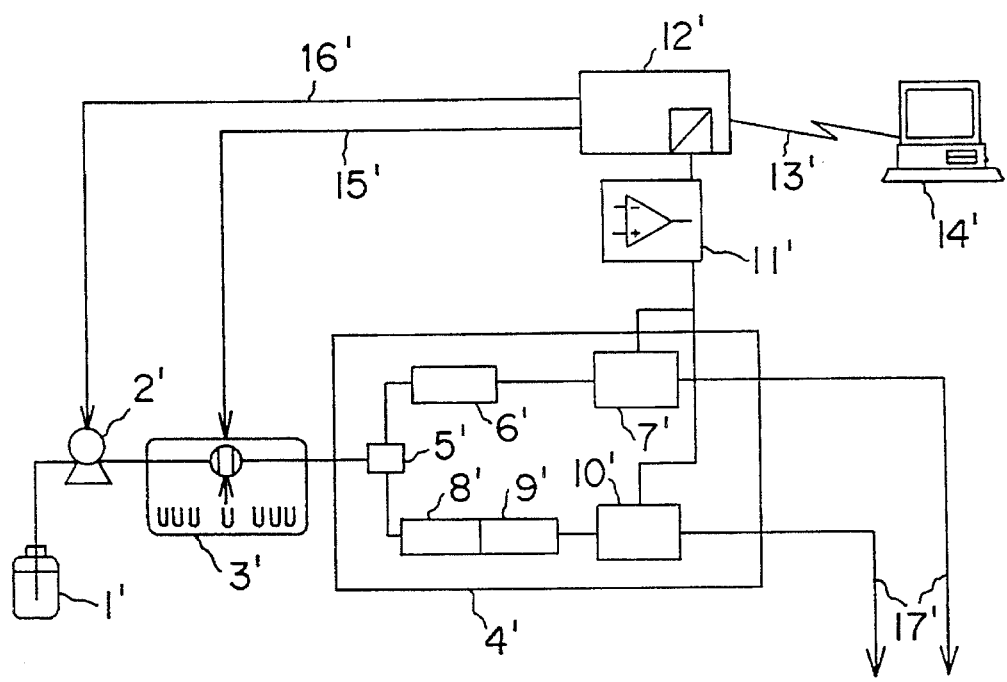
FIG. 1 shows a flow-type assay apparatus for assaying D-lactic acid and L-lactic acid.

The invention provides the apparatus and method for assaying the L- (or D-) optical isomers.

1. A method of assaying the L- and D-optical isomers as occurring in a sample which comprises:
(1) the step of assaying the L- (or D-) optical isomer as occurring in said sample; and
(2) the step of causing conversion of the L-optical isomer and D-optical isomer in said sample in the presence of a L-dehydrogenase and a D-dehydrogenase of said compound and oxidized coenzyme and then assaying the L- (or D-) optical isomer after said conversion.

2. A method of item 1, wherein said step of assaying the L- (or D-) optical isomer as occurring in said sample comprises oxidizing the L- (or D-) optical isomer using an oxidase for said L- (or D-) optical isomer and detecting the change in the concentration of an electrochemically active substance as resulting from the reaction involving said oxidase.

3. A method of item 1, wherein, in step (2), said conversion of L-optical isomer and D-optical isomer in the sample is performed in a reactor containing an immobilized L-dehydrogenase and an immobilized D-dehydrogenase.

4. A method of item 1, wherein said step of assaying the L- (or D-) optical isomer as occurring in said sample comprises oxidizing the L- (or D-) optical isomer using an oxidase for said L- (or D-) optical isomer and detecting the change in the concentration of electrochemically active substance as resulting from the reaction involving said oxidase.

5. A method of item 1, wherein said step of assaying the (L- or D-) optical isomer as occurring in said sample comprises oxidizing the L- (or D-) optical isomer using an oxidase for said L- (or D-) optical isomer and detecting the change in the concentration of hydrogen peroxide produced or oxygen consumed as resulting from the reaction involving said oxidase by an amperometric method using electrode.

6. A method of item 1, wherein in said step (2), said converting reaction between L- and D-optical isomer is conducted in a solution containing L-dehydrogenase and D-dehydrogenase.

7. A method of item 1, wherein said L- and D-optical isomers are L-lactic acid and D-lactic acid, and said L-dehydrogenase and D-dehydrogenase are L-lactate dehydrogenase and D-lactate dehydrogenase, respectively.

8. An apparatus for assaying the L- and D-optical isomers by the flow technique which comprises:

(i) means for injecting the sample into a carrier being fed from upstream;
(ii) a reactor containing said dehydrogenase for D-optical isomer and dehydrogenase for L-optical isomer each in immobilized form and
(iii) an immobilized oxidase for the L- (or D-) optical isomer and an electrode for detecting the change in the concentration of an electrochemically active substance as resulting from the oxidation of the L- (or D-) optical isomer in the sample by the action of the immobilized oxidase for said L- (or D-) optical isomer, and
(iii) being disposed downstream from (ii).

9. An apparatus of item 8 which further comprises means for stopping the feeding of said carrier or reducing the rate of flow of said carrier in a state such that the carrier containing the sample remains in contact with the D-dehydrogenase and L-dehydrogenase each in immobilized form.

10. An apparatus of item 8 which further comprises, upstream of said reactor, an immobilized oxidase for L- (or D-) optical isomer and an electrode for detecting the change in the concentration of an electrochemically active substance as resulting from the oxidation of L- (or D-) optical isomer in the sample by the action of the immobilized oxidase for the L- (or D-) optical isomer.

11. An apparatus of item 8, wherein the L- and D-optical isomers are L-lactic acid and D-lactic acid, respectively, and wherein said L-dehydrogenase and D-dehydrogenase are L-lactate dehydrogenase and D-lactate dehydrogenase, respectively.

12. A method of assaying the D- and L-optical isomers as occurring in a sample which comprises the processes of (1) contacting the sample and oxidised coenzyme with an enzyme system containing a D-dehydrogenase and a L-dehydrogenase to thereby cause conversion of the D-optical isomer and L-optical isomer as occurring in said sample and (2) detecting electrochemically the change in the concentration of an electrochemically active substance as resulting from the oxidation of the L- (or D-) optical isomer in the sample by the action of an oxidase for the L- (or D-) optical isomer, wherein the method comprises the steps of:

(a) in process (2), obtaining a working curve 1 showing the relation between the concentration of the L- (or D-) optical isomer and the output value in electrochemical detection using standard solutions of the L- (or D-) optical isomer as samples,
(b) performing process (1) using standard solutions of the L- (or D-) optical isomer as samples and subsequently performing process (2) to thereby obtain a working curve 2 showing the relation between the concentration of the L- (or D-) optical isomer and the output value in electrochemical detection,
(c) performing process (1) using standard solutions of the D- (or L-) optical isomer as samples and subsequently performing process (2) to thereby obtain a working curve 3 showing the relation between the concentration of the D- (or L-) optical isomer and the output value in electrochemical detection, then
(d) further performing process (2) using the assay sample to obtain an output value 1,
(e) performing process (1) using the assay sample and subsequently performing process (2) to obtain an output value 2,
and calculating the content of the D- and L-optical isomers in the assay sample based on the output values 1 and 2 and the working curves 1, 2 and 3.

13. A method of item 12, wherein the D-dehydrogenase and L-dehydrogenase are both immobilized on a support and packed in a reactor and wherein the carrier feeding is stopped or the rate of carrier flow is reduced for a certain period of time in a state such that oxidized coenzyme and the sample remain in contact with the immobilized dehydrogenases.

14. A method of item 12, wherein two parallel paths each comprising the oxidase for L- (or D-) optical isomer, which is in an immobilized form, and an electrode are used and wherein, in one of the paths, the L- (or D-) optical isomer originally occurring in the sample is assayed using the immobilized oxidase for L- (or D-) optical isomer and, in the other path, an immobilized enzyme containing the D-dehydrogenase and L-dehydrogenase is disposed in a position upstream of the immobilized oxidase for L- (or D-) optical isomer and assaying the L- (or D-) optical isomer after conversion of the D-optical isomer and L-optical isomer as caused by the D-dehydrogenase and L-dehydrogenase.

15. A method of assaying the D- and L-optical isomers which comprises performing two assays by using the apparatus as defined in item 8, one in the presence of oxidized coenzyme and the other in the absence of oxidized coenzyme, by contacting a sample with a D-dehydrogenase and a L-dehydrogenase each in an immobilized form.

16. A method of assaying the oxidation product derived from a L- (or D-) optical isomer and the L- and D-optical isomers as occurring in a sample which comprises the steps of:

(1) assaying the L- (or D-) optical isomer as occurring in said sample, (2) causing conversion of the L-optical isomer and D-optical isomer in the sample in the presence of a L-dehydrogenase and a D-dehydrogenase of said optical isomers and oxidized coenzyme and subsequently assaying the L- (or D-) optical isomer after said conversion, and (3) contacting the sample with a L-dehydrogenase (or D-dehydrogenase) in the presence of reduced coenzyme to thereby convert said oxidation product to the L- (or D-) optical isomer and then assaying the L- (or D-) optical isomer.

17. A method of item 16, wherein the step of assaying the L- (or D-) optical isomer comprises oxidizing the L- (or D-) optical isomer using an oxidase for the L-optical isomer (or oxidase for D-optical isomer) and detecting the change in the concentration of an electrochemically active substance as resulting from the reaction involving said oxidase.

18. A method of item 17, wherein said electrochemically active substance is hydrogen peroxide the concentration of which increases upon the oxidase-involving reaction, or oxygen the concentration of which decreases upon said reaction.

19. A kit comprising:
(1) a reagent comprising L-dehydrogenase and D-dehydrogenase of optical isomers and oxidized coenzyme to cause the conversion of L-optical isomer and D-optical isomer, and/or
(2) a reagent comprising L-dehydrogenase (or D-dehydrogenase) of the optical isomers and reduced coenzyme to convert an oxidized-form of the optical isomer in a sample into L- (or D-) optical isomer.

20. An apparatus of item 3, wherein the immobilization of the D-dehydrogenase and L-dehydrogenase is conducted by reacting a support having hydroxyl groups with an aminosilane reagent to convert the hydroxyl groups to aminosilane groups, reacting the amino group portions of the aminosilane groups formed on the surface of the support with a polyfunctional aldehyde to bond the polyfunctional aldehyde thereto, and bonding D-dehydrogenase and L-dehydrogenase to the polyfunctional aldehyde.

In the following, the present invention is described in further detail taking D-lactic acid and L-lactic acid as examples of the D- and L-optical isomers, and D-lactate dehydrogenase (D-LDH) and L-lactate dehydrogenase (L-LDH) as examples of the D-dehydrogenase and L-dehydrogenase, respectively. It goes without saying that this mode of practice is by no means limitative of the scope of the present invention.

In the following, the case of assaying L-lactic acid and D-lactic acid by assaying L-lactic acid is described. D-Lactic acid can be assayed by employing "D-lactic acid" in lieu of "L-lactic acid", and "D-lactate oxidase" in lieu of "L-lactate oxidase".

In the specification, "(or D-)" in the expression of "L- (or D-) optical isomer" indicates that the substance determined directly is a D-isomer, not a L-isomer.

The reactions in which D-LDH and L-LDH are respectively involved are shown below.

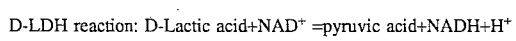

D-LDH reaction: D-Lactic acid+NAD$^+$ =pyruvic acid+NADH+H$^+$

L-LDH reaction: L-Lactic acid+NAD$^+$=pyruvic acid+NADH+H$^+$

Both the reactions are reversible. For both enzymes, however, the equilibrium is favorable for the formation of lactic acid and NAD. Therefore, even when the sample is contacted with a large amount of D-LDH in the presence of NAD, transformation to pyruvic acid hardly takes place.

The present inventors found, however, that when the sample is contacted with a mixture of D-LDH and L-LDH, L-lactic acid in the sample is converted to D-lactic acid and D-lactic acid to L-lactic acid and, after a sufficient time, an equilibrium is finally attained between D-lactic acid and L-lactic acid in a ratio of 1:1. When L-lactic acid is contacted with D-LDH and L-LDH, the amount of L-lactic acid decreases. This phenomenon can be construed as the result of oxidation of lactic acid to pyruvic acid and regeneration of lactic acid from said pyruvic acid and NADH under the catalytic action of D-LDH and L-LDH occurring in the neighborhood.

An interesting fact was further found. Namely, even in a mixture sample containing D-lactic acid and L-lactic acid, the rates of conversion of the optically active lactic acid isomers are independent. Thus, the sample and NAD are contacted with D-LDH and L-LDH immobilized on a support in close vicinity to each other, and the amount of L-lactic acid after contacting with the immobilized enzymes is detected. L-Lactic acid can be detected using, for example, an immobilized L-lactate oxidase and a hydrogen peroxide electrode. When samples containing L-lactic acid alone in various concentrations are contacted with said enzymes, a concentration range is observable in which a linear relation is found between the L-lactic acid concentration and the output value from the hydrogen peroxide electrode. Therefore, one point in this concentration range is selected and D-lactic acid is added in various concentrations to an L-lactic acid solution at said concentration point, whereby another working curve (hereinafter, L1) can be obtained. Then, using samples containing D-lactic acid alone in various concentrations, a further working curve (hereinafter, L2) is obtained which shows the relation between the D-lactic acid concentration and the output electric current value. In this case, the gradient of L1 is identical with that of L2, and the intercept of L1 is equal to the output current value when L-lactic acid is subjected to contact at the corresponding concentration. In this system, substitution of L-lactic acid for D-lactic acid and vice versa gives the same results.

This indicates that the relations between the D-lactic acid concentration and L-lactic acid concentration and the output current value are independent of each other and that even when D-lactic acid and L-lactic acid are contained mixedly in an actual sample, the D-lactic acid content can be calculated if the concentration of L-lactic acid originally contained is separately determined.

Unless conducted under the same conditions, this reaction is not reproducible. Once the reaction conditions have been established, however, D-LDH and L-LDH may be used either in a solution form or in an immobilized form.

The rates of conversion of D-lactic acid and L-lactic acid naturally increase as the time of contact the sample and NAD with D-LDH and L-LDH is prolonged. After a sufficiently long reaction time, D-lactic acid and L-lactic acid finally arrive at an equilibrium to give a racemic mixture, when the reaction apparently stops. Therefore, when a solution of D-LDH and L-LDH is used as such, it is more practical to perform assays in a state in which an equilibrium has been attained and the reaction has stopped than to specify the reaction conditions.

On the other hand, when D-LDH and L-LDH are used in immobilized form, a fairly long time is required for the reaction to arrive at an equilibrium. Such mode of use is thus not suited for continuous assaying of many samples in a very short time but makes it possible to perform assays under constant reaction conditions, hence to assay D-lactic acid and/or L-lactic acid exactly and precisely even in a non-equilibrium state.

The activity of LDH is generally defined by determining the rate at which lactic acid is formed from pyruvic acid, The proportion of L-LDH relative to D-LDH can be varied within the activity ratio range of about 1/10 to about 20, preferably about ½ to about 10, more preferably about ½ to about 5, and most preferably about 1 to about 5. For said reaction, NAD is required but can be recycled, hence it is used in an amount of about 1/20 to about 10 times, preferably about 1/10 to about 5 times, more preferably about 1/5 to about 4 times, the concentration of lactic acid in the sample.

At an L-LDH/D-LDH ratio of about 1 up to about 5, the equilibrium reaction always proceeds to a constant D-lactic acid/L-lactic acid ratio irrespective of whether the sample contains only one of D-lactic acid and L-lactic acid or both of them in any ratio. Thus, the D-lactic acid/L-lactic acid ratio becomes approximately 1:1.

The enzyme L-LDH to be used may be of any of various origins, for example bovine, swine, rabbit or chicken viscera or muscles. The enzyme D-LDH may be a product derived from a microorganism such as a lacto-bacillus or some other bacterial species. As for the origin of LOD, Pediococcus-derived LOD is known. LOD species of other origins may of course be used.

In the following, the present invention is described in two aspects thereof, aspect I (assay of D-lactic acid and/or L-lactic acid) and aspect II (assay of pyruvic acid and D-lactic acid and/or L-lactic acid).

*Aspect I

Although the reactions respectively involving D-LDH and L-LDH are already known in the art, the finding that D-lactic acid, for instance, can be converted to L-lactic acid efficiently by using both the enzymes combinedly is a quite unexpected one.

Based on this new finding, D-lactic acid can be converted to L-lactic acid efficiently. When this step is combined with a selective assay method for L-lactic acid, D-lactic acid and L-lactic acid can be assayed.

A method of assaying D-lactic acid and L-lactic acid in which said step is combined with a selective assay method for L-lactic acid is described below in further detail.

In Aspect I of the invention, the equilibrium reaction between lactic acid and pyruvic acid, which is catalyzed by lactate dehydrogenase in the presence of NAD, is much favorable for the formation of lactic acid, as mentioned above, even when pyruvic acid coexists, hence the amount of pyruvic acid is negligible as compared with lactic acid. Therefore, the results of the lactic acid assay in accordance with Aspect I of the invention are substantially free from the influence of pyruvic acid.

The method of determining the D-lactic acid and L-lactic acid contents which comprises bringing D-lactic acid and L-lactic acid into an equilibrium state, when immobilized D-LDH and L-LDH are used, requires a long time for effecting the reaction, hence unsuited for continuous assaying. In general enzymatic reactions, a linearity can be established between the reaction time and the conversion rate only when the substrate conversion rate is 20% or less. Therefore, in an enzyme amount used for immobilization, the sensitivity increases substantially linearly as the contact time is prolonged until the conversion rate reaches 20%. Thereafter, however, the reaction rate decreases gradually and therefore, even when the contact time is prolonged by decreasing the carrier flow rate, the effect obtainable thereby decreases. When assaying is performed, even in the case of stopping the flow or reducing the flow rate, in a time within a range such that the conversion rate reaches about 80%, the assaying can be finished practicably in a short period of time.

An embodiment of the invention in which the flow is stopped or the flow rate is reduced will be described later.

For prolonging the time of contact of the sample and NAD with immobilized D-LDH and L-LDH, the flow rate may be reduced in a state such that the sample and NAD are in contact with immobilized D-LDH and L-LDH. If the flow is stopped in a state in which the sample is in contact with immobilized D-LDH and L-LDH to thereby allow the reaction to progress for a sufficiently long time, a conversion rate of 100% can possibly be obtained. In this case, a racemic mixture of D-lactic acid and L-lactic acid (1:1) is formed.

In accordance with the invention, assaying can be performed using immobilized D-LDH and L-LDH under constant conditions, hence exact assaying is possible even when the conversion rate is less than 100%.

L-Lactic acid in a sample must be assayed by a method by which the assay is not affected by other substances possibly occurring in the sample than L-lactic acid, for example D-lactic acid and NAD. For this purpose, the assay method which uses L-lactate oxidase can be employed.

The reaction in which LOD is involved is shown below:

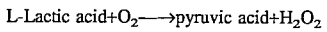

L-Lactic acid+$O_2$ ⟶ pyruvic acid+$H_2O_2$

This reaction is not influenced by coexisting D-lactic acid and/or NAD. L-Lactic acid can be assayed by detecting the produced hydrogen peroxide or consumed oxygen or through the intermediary of the so-called mediator, which is an electron transmitter capable of causing direct charge transfer between itself and LOD, for example dichloroindophenol, potassium ferricyanide or bezoquinone, in lieu of oxygen.

The L-lactic acid concentration in the sample is determined in advance by this method and then, after the above-mentioned conversion of D-lactic acid to L-lactic acid, and the resulting L-lactic acid concentration is determined, whereby D-lactic acid can be assayed based on the difference in L-lactic acid concentration. Since even when the reaction has not yet progressed to an equilibrium between D-lactic acid and L-lactic acid, the rate of formation of L-lactic acid from D-lactic acid (rate of decrease in L-lactic acid concentration) per unit time is constant, it is possible to assay D-lactic acid and L-lactic acid by comparing the L-lactic acid concentration after reaction with that before reaction provided that the enzymatic reaction time is kept constant.

In assaying L-lactic acid using L-lactate oxidase, the decrease in the amount of oxygen or the increase in the amount of hydrogen peroxide should suitably be detected. For this purpose, methods are available which comprise absorbance measurement in the visible region, for example the method which uses peroxidase and 2,2'-azinodi(3-ethylbenzothiazoline)-6-sulfonic acid or 4-aminoantipyrin (Trinder method). Absorbance measurement in the visible region is less affected by turbidity as compared with absorbance measurement in the ultraviolet region.

An electrochemical method may also be used which measures the change in the concentration of an electrochemically active substance such as oxygen or hydrogen peroxide after conversion of said change to an electric current value. This method is not affected by turbidity of the sample or coloring matter contained therein and can be performed more easily as compared with the method using a spectrophotometer, hence is preferred.

In particular, a highly sensitive, simple and easily operable apparatus can be constructed by immobilizing L-lactate oxidase with which relatively high reaction rates can be obtained. The change in the concentration of oxygen or hydrogen peroxide can be determined by a colorimetric or electrochemical method. Among them, the electrochemical method is preferred.

various known oxygen electrodes, for example of the Garvani type or Clark type, may be used as the oxygen electrode for measuring the consumption of oxygen. The electrode for hydrogen peroxide determination is preferably built in a cell. The cell may be made of such a nonconductive material as acrylic resin, fluororesin, vinyl chloride resin or glass or such a conductive material as stainless steel, gold, platinum or silver, or a combination of these. When a conductive material is used, care should be taken to electrically isolate the same from the electrode system.

As examples of the electrode, there may be mentioned two-electrode systems comprising a working electrode and a counter electrode and three-electrode systems comprising a working electrode, a reference electrode and a counter electrode. The electrodes can be formed by implanting a conductive substance into the measurement cell bottom, vapor-depositing a metal on the cell wall inside surface, metal plating from solution, nonelectrolytic plating, or printing, for instance. The counter electrode and reference electrode are desirably positioned in the vicinity of the working electrode so that the resistance of the solution can be minimized.

The material of the working electrode may be any of those materials generally used in electrochemical measurements, such as metals, e.g. gold, platinum and silver, glassy carbon, carbon paste and the like.

The counter electrode may be made of such a conductive material as stainless steel or any of those materials mentioned above with respect to the working electrode. The solution-contacting portion of the cell may be constructed by using a conductive material such as stainless steel and may also serve as the counter electrode.

As the reference electrode, there may be mentioned, for example, such conventional ones as silver-silver chloride reference electrode and saturated calomel reference electrode.

D-LDH, L-LDH and LOD can be used in a solution form or in a form immobilized on an appropriate support. When used in a solution form, the enzymes can be added to the sample in required amounts. In that case, however, the enzymes can be used only once and then must be discarded, hence the assay cost increases. When used in an immobilized form, the enzymes can be used repeatedly with the advantage that the reaction conditions therefor can be adjusted with ease.

D-LDH and L-LDH can be immobilized by any of the conventional methods such as the adsorption method, chemical coupling or covalent binding method, and entrapping method. As examples of the support to be used for enzyme immobilization, there may be mentioned diatomaceous earth, calcined diatomaceous earth, silica gel, glass beads, alumina, ceramic materials, carbon, activated carbon, molecular sieves, silicone rubbers, cellulose, agarose, amino acid-based polymers, and the like. As regards the form of immobilized enzyme, the enzymes may be immobilized on a film covering the electrode surface, or immobilized on a support and packed in a reactor in the form of a column, for instance, or immobilized in the surface of a reactor in the form of a membrane or hollow fiber, for instance. In particular, when a support bearing the enzymes immobilized thereon is packed in a column, the time of contact between the sample and each immobilized enzyme can advantageously be prolonged to thereby increase the conversion rate. While a column with a larger capacity is advantageous in that the support can be packed therein in larger amounts, such column is disadvantageous in that a longer assay time is required. A desirable capacity is about 10 to 500 μl. The column is made of acrylic resin, fluororesin, vinyl chloride resin, glass, stainless steel or some other metal, or a combination of these. In an example of the chemical coupling method, an amino group is preferably introduced into the support surface by means of an aminosilane coupling agent and, after formylation using a multifunctional aldehyde such as glutaraldehyde, the enzyme or enzymes are brought into contact with the support for immobilization. More specifically, a support having hydroxyl groups, such as diamaceous earth, calcined diatomaceous earth (fire brick, etc.), cellulose, porous glass, silica gel or acid clay is treated for conversion of hydroxyl groups to aminosilane, and reacted with a polyfunctional aldehyde, whereby the polyfunctional aldehyde is bonded to the amino groups formed on the surface of the support to introduce the aldehyde groups onto the support. Subsequently enzyme is bonded to the aldehyde groups for immobilization. Such immobilized dehydrogenase or oxidase is preferred in view of operational efficiency and less decrease of enzyme activity. Of these supports, preferred are diatomaceous earth, calcined diatomaceous earth, porous glass, silica gel, acid clay and the like which comprise silicate. More preferred are diatomaceous earth, calcined diatomaceous earth.

The conversion of hydroxyl groups to aminosilane can be done by bringing a reagent such as 3-aminopropyltriethoxysilane, 3-aminoethyltrimethoxysilane or the like into contact with the support in a solvent such as anhydrous benzene, toluene or the like. Useful polyfunctional aldehydes include glutaraldehyde, glyoxal, succinyldialdehyde, etc.

Since the conversion reaction of lactic acid in the sample is based on the D-LDH reaction and L-LDH reaction mentioned above, it is desirable that the sample and NAD can contact with D-LDH and L-LDH substantially simultaneously. More specifically, a membrane supporting D-LDH immobilized thereon is superposed on a membrane supporting L-LDH immobilized thereon, or a support with D-LDH immobilized thereon is mixed with a support with L-LDH immobilized thereon, or a D-LDH solution and an L-LDH solution are blended and the mixed solution is applied to a support or membrane for immobilization, for instance. The immobilization on the electrode surface is not necessarily satisfactory for effecting the lactic acid conversion reaction, however, since D-LDH and L-LDH are generally low in activity and the corresponding enzyme reactions are slow. Therefore it is desirable to immobilize the enzymes on a support for packing into a reactor such as a column.

In immobilizing LOD, the adsorption method, chemical coupling method, and entrapping method, for instance, can be employed as in the above-mentioned case of D-LDH and L-LDH, for packing in a reactor such as a column. It is also possible to obtain a membrane containing immobilized LOD using a crosslinking agent such as glutaraldehyde, formaldehyde or succinaldehyde and attach the membrane thus obtained to an electrode. In the enzyme immobilization, LOD may be crosslinked by further adding a protein such as albumin, globulin or gelatin.

NAD may be added either to the sample or to the carrier (buffer solution). When NAD is added to the sample, it is added preferably to a concentration of about 2 mM to about 20 mM and this mode of addition is suited for cases where the number of samples is small. In the case of addition to the carrier by a flow technique, NAD is always in a state of contact with immobilized D-LDH and L-LDH and the efficiency of its use is higher than in the case of addition to the sample, hence NAD is preferably added to a concentration of about 1 mM to about 10 mM. This method of addition is suited for the case where the number of samples is large.

The level of addition of NAD can be reduced with the prolongation of the time of contact of the sample and NAD with immobilized D-LDH and L-LDH.

Furthermore, since the rates of reaction on immobilized D-LDH and L-LDH are relatively slow, means for stopping the carrier feeding or reduce the rate of carrier flow for a certain period of time to thereby maintain the sample and NAD in contact with immobilized D-LDH and L-LDH for said period of time so that a sufficient level of sensitivity can be obtained and the conversion rate can be increased to attain a state close to equilibrium.

In the case of stopping the carrier feeding for a period, the carrier feed stopping should recommendably be started after entrance of the whole amount of the sample into the reactor containing immobilized D-LDH and L-LDH while the period of stoppage may be selected within a range in which the rapidness of assay, which is a feature of the present invention, will not be sacrificed. From the practical viewpoint, said period is desirably within 5 minutes so that each assay process can be finished in a short time.

In the case of reducing the carrier flow rate for a period, it is necessary to reduce the flow rate at least before the sample-carrier mixture front leaving the reactor containing immobilized D-LDH and L-LDH and preferably before said sample-carrier mixture front having passed through an entry port of said reactor. As in the above case, the flow rate reduction period should desirably be within 5 minutes so that each assay procedure can be finished in a short time.

For stopping the carrier feeding or reducing the carrier flow rate for a certain period in the reactor containing immobilized D-LDH and L-LDH, the control value for the pump flow rate may suitably be modified, for example, at the time of arrival at the immobilized D-LDH and L-LDH based on the time period between the time of sample injection and the time of arrival at the immobilized D-LDH and L-LDH as determined by calculation based on the length and diameter of the piping from the sample injection port to said reactor and the feeding rate at the pump or by preliminary actual measurement, for instance.

As a typical method therefor, there may be mentioned, for example, the method comprising controlling the pump flow rate via a D/A converter using a specific electronic circuit or a computer and at the same time exactly monitoring the time from initiation of sample injection to arrival at the immobilized enzymes mentioned above.

It is also possible to connect the reactor containing immobilized D-LDH and L-LDH to a loop portion connected to a selector valve and retain the sample in said reactor for a certain period to thereby attain a high conversion rate.

As the carrier to be fed, there may be mentioned buffer solutions having a pH of about 7, which is suitable for D-LDH, L-LDH and LOD, and incapable of exerting any electrochemical influence on the electrodes, for example phosphate buffer.

*Aspect II

In the following, additions and modifications to Aspect I are described in the main.

The reactions respectively involving D-LDH and L-LDH are as follows.

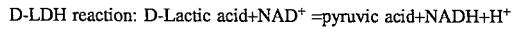

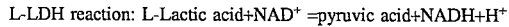

Both the reactions are reversible. For each enzyme, however, the equilibrium is favorable for the formation of lactic acid and $NAD^+$. Therefore, L-LDH causes almost 100% conversion of pyruvic acid to L-lactic acid in the presence of NADH. L-LDH causes conversion of L-lactic acid to pyruvic acid very slowly even mixed with $NAD^+$. The same applies to D-LDH as well.

Unexpectedly, however, the present inventors found that when lactic acid is contacted with L-LDH and D-LDH in the presence of NAD, an equilibrium state in which the ratio between D-lactic acid and L-lactic acid is approximately 1:1 (racemization) is arrived at. Thus, when these reactions are combined with a detection method specific to L-lactic acid, L-lactic acid, D-lactic acid and pyruvic acid in samples can be assayed.

In the following, (a) L-lactic acid assaying, (b) D-lactic acid assaying and (c) pyruvic acid assaying are described one by one.

(a) L-Lactic acid: As mentioned above, L-lactic acid in the sample is specifically assayed using LOD.

(b) D-Lactic acid assay: The sample is contacted with L-LDH and D-LDH in the presence of NAD for approximate racemization, followed by L-lactic acid assay. The total lactic acid content in the sample can then be calculated from the results of said assay. The value for D-lactic acid can be obtained by subtracting the L-lactic acid concentration obtained in (a) from said total lactic acid content.

The racemization in this step (b) can also be carried out by immobilizing L-LDH and D-LDH on a support using a crosslinking agent or the like. Such use of the LDHs in immobilized form is economical since the immobilized enzymes can be used repeatedly for analysis. On the other hand, when the LDHs are used in solution form, the enzymatic reaction rates are rapid, hence the time of analysis becomes short. Therefore, for assaying a large number of samples at a time, the LDHs are preferably used in the form of an aqueous solution.

(c) Pyruvic acid assay: The sample is contacted with L-LDH in the presence of NADH for causing conversion of pyruvic acid to L-lactic acid and the L-lactic acid is then assayed. The assay value corresponds to the sum of that portion of L-lactic acid originally occurring in the sample and that portion of L-lactic acid formed from pyruvic acid. Therefore, the pyruvic acid content in the sample can be calculated by subtracting the L-lactic acid content obtained in step (a) from that total value.

The reaction which forms L-lactic acid from pyruvic acid in the presence of L-LDH can readily proceed and therefore L-LDH is required only in an amount about one tenth the amount required in the racemization reaction in the above step (b). Since NADH is consumed in this L-LDH reaction in an amount equimolar to L-lactic acid, NADH is used in an amount larger than that of pyruvic acid in the sample, preferably in an amount of 2 moles or more per mole of pyruvic acid in the sample.

When L-LDH and D-LDH are used in a solution form, in the practice of the invention, LOD is used in an immobilized form. This is because the use in solution form LOD has the following problems.

First, when LOD in solution form coexists L-LDH, D-LDH and NAD, L-lactic acid alone decreases as a result of consumption thereof by LOD and this induces the racemization reaction, whereby D-lactic acid is proportionally converted to L-lactic acid. Finally, the whole amount of lactic acid is converted to hydrogen peroxide and pyruvic acid. Secondly, when LOD coexists with L-LDH and NADH, the pyruvic acid formed from L-lactic acid reacts with NADH and the recycle reaction leading to the formation of L-lactic acid. As a result, hydrogen peroxide and pyruvic acid are formed until there remains no more NADH. In such a case, exact assay of L-lactic acid is impossible. Therefore, it unpractically becomes necessary to modify the pH of the LDH-containing reaction mixture or heat said mixture for enzyme inactivation so that the recycle can be inhibited.

In the case of immobilized LOD, too, such problems as mentioned above are theoretically predictable.

However, the rate of the reaction involving LOD is more rapid as compared with L-LDH and D-LDH and therefore, when the LOD is used in an immobilized form, exact assay of L-lactic acid can be performed by contacting the reaction mixture after completion of the reactions involving L-LDH and D-LDH with immobilized LOD for a period sufficiently short for avoiding such trouble-making recycle reaction as mentioned above. This is because, in that case, the reactions involving the L-LDH and D-LDH added to the sample are negligible.

The immobilization of LOD can be effected in the same manner as in the case of L-LDH and D-LDH mentioned above.

As the oxygen electrode for determining the oxygen consumption, those oxygen electrodes already mentioned hereinabove can be used. The hydrogen peroxide electrode for determining the hydrogen peroxide formation may be any of known hydrogen peroxide electrodes in which carbon, platinum, nickel, palladium or the like is used as the anode base body and silver or the like is used on the cathode side. Generally, platinum is preferred as the anode because the overvoltage is low and a high sensitivity can be obtained. Those electrodes which have a selectively permeable membrane such as a polysiloxane, acrylic resin, protein or acetylcellulose membrane are preferred from the viewpoint of removal of interfering substances.

From the stability and precision viewpoints, the hydrogen peroxide electrode and oxygen electrode should preferably be of the three-electrode type comprising a working electrode, a counter electrode and a reference electrode, although they may be of the two-electrode type comprising a working electrode and a counter electrode.

In one embodiment of Aspect II of the present invention, L-lactic acid, D-lactic acid and pyruvic acid, for instance, can be assayed using an apparatus comprising immobilized LOD and an electrode.

More specifically, a working curve is first obtained using standards solutions prepared from L-lactic acid or a mixture of D-lactic acid and L-lactic acid with a known proportion of L-lactic acid. Using the thus-obtained working curve for L-lactic acid, the L-lactic acid concentration in the sample is determined.

Then, the sample is treated with L-LDH and NADH for the conversion of pyruvic acid to L-lactic acid. The reaction mixture is then contacted with immobilized LOD and, based on the resulting electrochemically active substance (e.g. hydrogen peroxide), the total content of L-lactic acid and pyruvic acid is determined.

Finally, the racemization reaction is performed in the presence of L-LDH, D-LDH and NAD and, based on the L-lactic acid concentration in the reaction mixture, the sum of total lactic acid and pyruvic acid is determined. The L-lactic acid, D-lactic acid and pyruvic acid contents can each be calculated from the assay values mentioned above. On this occasion, when the sample and reagent enzyme are mixed in a ratio of 1:1, for instance, the L-lactic acid concentration is calculated by doubling the assay value after the racemization reaction.

In the practice of the invention, lactic acid and pyruvic acid each may be in the free acid form or in the form of a salt thereof, and the free acids as well as salts thereof may be used in preparing standard solutions. In particular, the lithium salt form is least hygroscopic, hence easy to handle. In assaying the three species, namely L-lactic acid, D-lactic acid and pyruvic acid by the method of the present embodiment, the standard solutions to be prepared are standard solutions of L-lactic acid alone, hence the time for preparing standard solutions and performing assay can be reduced. Organic acids are generally unstable and long-period storage thereof in solution form is difficult. High-purity reagents are expensive, in particular lithium D-lactate is very expensive. Lithium pyruvate is sparingly soluble and difficult to handle. In the practice of the embodiment, only standard solutions of lithium L-lactate alone are required; this makes the procedure simple and at the same time advantageous from the cost viewpoint.

The following assay apparatus may be mentioned as typical examples of aspect I.

A first apparatus is an assay apparatus (FIG. 1) using the flow technique. It divides the sample and NAD carried by a carrier such as a buffer solution into two streams and brings one into contact with L-lactate oxidase (6') for L-lactic acid assay. The other portion is contacted with D-LDH and L-LDH (8') for a certain specified period, and then is contacted with L-lactate oxidase (9') and L-lactic acid assaied after conversion reaction. The assaying can be performed rapidly and in a simple manner by dividing the flow in two directions, as shown in FIG. 1. It is also possible to perform two assays in two assay systems without branching carried flow containing the sample and NAD.

Figure 3:
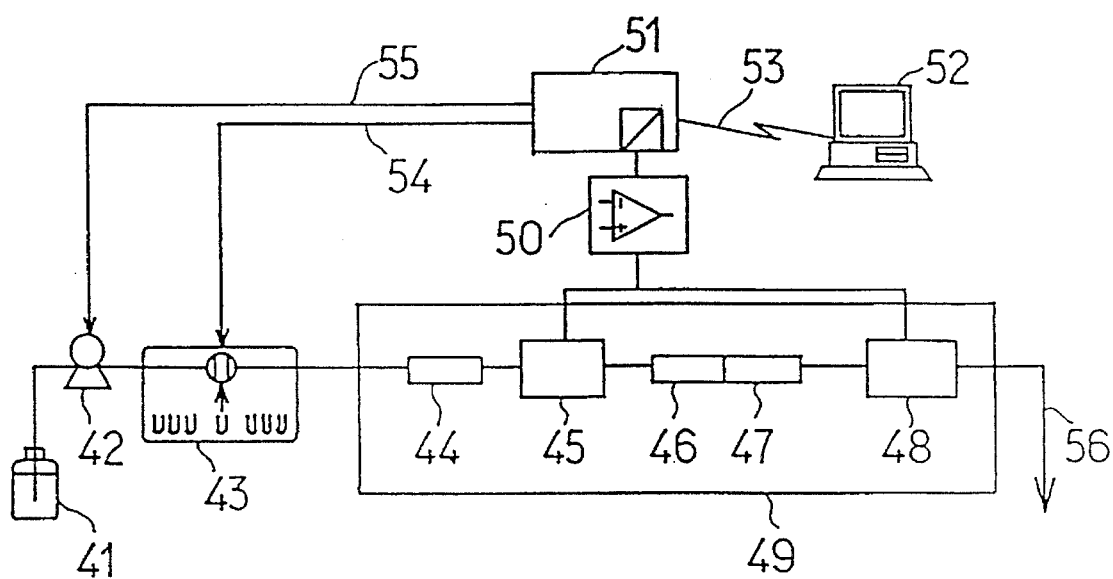
FIG. 3 shows another embodiment of the invention.

A second apparatus (FIG. 3) is an apparatus using the flow technique as constructed by connecting in series, in the order from upstream, a column containing immobilized L-lactate oxidase (LOD) (44), a hydrogen peroxide electrode (45), a column containing immobilized D-LDH and L-LDH (46), a column containing immobilized LOD (47) and a hydrogen peroxide electrode (48). The sample and NAD carried by a carrier such as a buffer solution are first contacted with the immobilized LOD (44) in the first column for detecting L-lactic acid, then with the immobilized D-LDH and L-LDH (46) in the second column for a certain specified period and finally with the immobilized LOD (47) in the third column for obtaining a detection value for L-lactic acid after conversion reaction.

Figure 2:
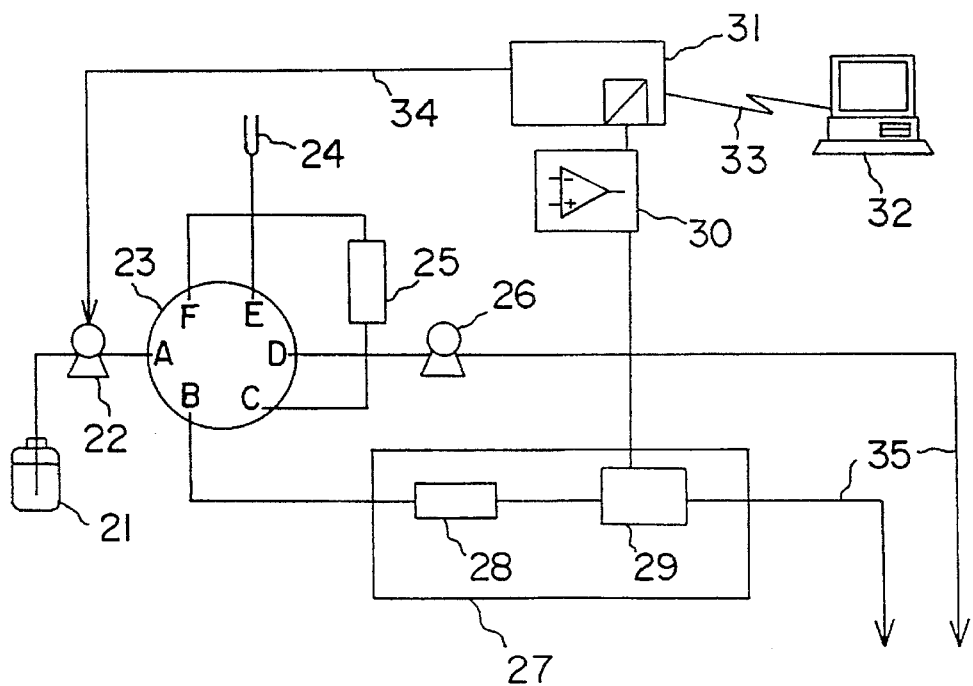
FIG. 2 shows another flow-type assay apparatus for assaying D-lactic acid and L-lactic acid.

A third apparatus (FIG. 2) is an assay apparatus which uses the flow technique and comprises a column containing immobilized D-LDH and L-LDH (25) and, downstream thereof, means for detecting L-lactic acid (27) comprising L-LOD (28) and electrode (29). For the case in which the sample is contacted with D-LDH and L-LDH (25) in the presence of NAD, namely L-lactic acid is assayed after conversion between L-lactic acid and D-lactic acid. And for the case in which NAD is absent, L-lactic acid is assayed without conversion reaction of isomers, namely L-lactic acid in the original sample is assayed. And based on both assay values obtained, the L-lactic acid and D-lactic acid are determined.

In performing assays using these apparatus, NAD may be added to the buffer solution or to the sample.

In actual assaying, working curves are first prepared respectively for D-lactic acid and L-lactic acid and a working curve is constructed based on the current values obtained.

Working curve 1 is a working curve for L-lactic acid as obtained by performing assays without conversion of D-lactic acid and L-lactic acid, namely by contacting the samples only with immobilized LOD either without passing through the column containing immobilized D-LDH and L-LDH or before passing therethrough or by assaying without causing NAD to contact with immobilized D-LDH and L-LDH. Under these conditions, injection of D-lactic acid gives no current value at all.

Working curve 2 is a working curve obtained from the current values after passage of L-lactic acid through the column containing immobilized D-LDH and L-LDH in the presence of NAD. In working curve 2, the proportion of hydrogen peroxide formed from L-lactic acid is low as compared with working curve 1 because of conversion of part of the L-lactic acid to pyruvic acid.

Working curve 3 represents the results obtained from standard solutions of D-lactic acid under the same conditions as in the case of working curve 2. In assaying a sample, electric current value 1 is obtained in the same step as in the case of working curve 1 and electric current value 2 is obtained in the same step as in the cases of working curve 2 and working curve 3.

The D-lactic acid and L-lactic acid concentrations are calculated as shown below by way of example. Current value 1 is applied to working curve 1 to calculate the L-lactic acid concentration. The L-lactic acid concentration obtained is applied to working curve 2 to calculate the L-lactic acid-due current value contributing to current value 2. The contribution of D-lactic acid can be determined by subtracting said L-lactic acid-due current value contributing to current value 2 from current value 2. The D-lactic acid concentration can be calculated by applying this D-lactic acid contribution to working curve 3.

After arriving at an equilibrium between D-lactic acid and L-lactic acid, working curve 2 and working curve 3 theoretically become identical to each other, the gradient being half that of working curve 1. Therefore, when determinations are made by the solution method with a sufficient reaction time after the reaction having arrived at an equilibrium, without immobilizing D-LDH and L-LDH, it is sufficient for the assay to determine L-lactic acid alone. For this purpose, detection is made using immobilized L-LOD and a hydrogen peroxide electrode alone. The working curve in this case is working curve 1 alone. In this case, however, two assay processes are necessary, one obtained for L-lactic acid by subjecting the sample as such to assaying the originally contained L-lactic acid in a sample and the other obtained for L-lactic acid after the equilibrium reaction. Since the assay value after the complete equilibrium reaction corresponds to the sum of equal amounts of L-lactic acid and D-lactic acid, the assay value for L-lactic acid is doubled to give the total content of L-lactic acid and D-lactic acid. The assay value for D-lactic acid can be obtained by subtracting the assay value obtained first for L-lactic acid from said total content.

The use of L-LOD (or D-LOD), D-LDH and L-LDH in immobilized form is advantageous, for example in that the enzymes can be used repeatedly and that the conditions for the enzyme reactions can be readily adjusted.

The method of enzyme immobilization, the mixing ratio between D-LDH and L-LDH, the mode of addition of NAD, the method of stopping the sample flow or reducing the flow rate, the method of assaying L-lactic acid, the hydrogen peroxide electrode and the oxygen electrode, among others, are the same as those mentioned with regard to Aspect I of the invention.

In the foregoing, the case in which the conversion reaction of L-lactic acid and D-lactic acid is carried out using immobilized D-LDH and L-LDH has been described in the main. The case where the conversion reaction can be conducted using D-LDH and L-LDH in the form of a solution.

When D-lactic acid is contacted with D-LDH and L-LDH in solution, L-lactic acid is also formed from the pyruvic acid formed and NADH, as already mentioned above.

When L-lactic acid is contacted with D-LDH and L-LDH, the L-lactic acid decreases and L-lactic acid is formed.

D- and L-optical isomers and dehydrogenases other than lactic acids and lactate dehydrogenases are shown below.

According to Table A, when D- and L-lactic acid, lactate dehydrogenase, NAD, pyruvic acid and L-lactate oxidase are replaced by a set of substances indicated in the second row or below of the table, other optical isomers and oxidized form substrate demonstrated in the left column of Table A can be assayed.

TABLE A

| Optical isomers | Dehydrogenase | Co-enzyme | Oxidized-form substrate | Oxidase |
|---|---|---|---|---|
| Lactic acid, pyruvic acid assay | D-lactic acid<br>L-lactic acid | D-Lactate dehydrogenase<br>L-Lactate dehydrogenase | NAD | Pyruvic acid | L-lactate oxidase |
| Glutamic acid, α-keto-glutaric acid assay | D-Glutamic acid<br>L-Glutamic acid | D-Glutamate dehydrogenase<br>L-Glutamate dehydrogenase | NAD | α-Keto-glutaric acid | L-Glutamate oxidase |
| Leucine, α-keto-valeric acid assay | D-Leucine<br>L-Leucine | D-Leucine dehydrogenase<br>L-Leucine dehydrogenase | NAD | α-Keto-valeric acid | Amino acid oxidase |
| Galactose, galacto-δ-lactone assay | D-Galactose<br>L-Galactose | D-Galactose dehydrogenase<br>L-Galactose dehydrogenase | NADP | Galacto-δ-lactone | D-Galactose oxidase |

EXAMPLES

The following examples illustrate the invention in further detail. Of course, they are by no means limitative of the scope of the invention.

For all the solutions having a pH of 7.0 as used in the following examples, 100 mM sodium phosphate buffer is used as the solvent.

Example 1

(1) Production of a column containing immobilized L-lactate oxidase (LOD)

A firebrick powder (calcined diatomaceous earth-type; 30–60 mesh; 150 mg) is thoroughly dried, immersed in a 10% solution of γ-aminopropyltriethoxysilane in anhydrous toluene for 1 hour, then thoroughly washed with toluene and dried. The aminosilane-modified carrier is immersed in a 5% glutaraldehyde solution for 1 hour and then thoroughly washed with distilled water, followed by substitution with 100 mM sodium phosphate buffer (pH 7.0). The buffer is removed as far as possible. A solution (200 μl) of L-lactate oxidase (Sigma Chemical Company) (50 units/ml) in 100 mM sodium phosphate buffer (pH 7.0) is brought into contact with the formylated firebrick. The mixture is allowed to stand at 0° C. to 4° C. for 1 day for enzyme immobilization. The thus-obtained immobilized enzyme-bearing carrier support is packed into an acrylic resin column (3.5 mm in inside diameter, 30 mm in length) to give a column containing immobilized L-lactate oxidase (L-LOD).

(2) Production of a hydrogen peroxide electrode

The side face of a platinum wire with a diameter of 2 mm is covered with heat-shrinking Teflon and one end of the wire is smoothed using a file and #1500 emery paper. Using this wire as a working electrode, a platinum plate (1 cm×1 cm) as a counter electrode and a saturated calomel electrode as a reference electrode, electrolytic treatment is performed in 0.1M sulfuric acid at +2.0 V for 10 minutes. The platinum wire is then thoroughly washed with water, dried at 40° C. for 10 minutes, immersed in a 10% solution of γ-aminopropyltriethoxysilane in anhydrous toluene for 1 hour and then washed with toluene. Glutaraldehyde is added to a solution of 20 mg of bovine serum albumin (Sigma Chemical Co., Fraction V) in 1 ml of distilled water in an amount of a glutaraldehyde concentration of 0.2%. A 5-μl portion of the resulting mixture is quickly placed on the platinum wire prepared as mentioned above, followed by drying and curing at 40° C. for 15 minutes, whereby a membrane selectively permeable to hydrogen peroxide is formed, which can serve to eliminate adverse effects of interfering substances such as ascorbic acid. The platinum wire thus processed is used as the working electrode of a hydrogen peroxide electrode.

A silver-silver chloride (Ag/AgCl) electrode is used as a reference electrode, and a conductive piping as a counter electrode.

(3) Production of a column containing immobilized D-LDH and L-LDH

The same formylated calcined diatomaceous earth (firebrick) as used for immobilizing L-lactate oxidase is contacted with 500 μl of a solution of D-lactate dehydrogenase (D-LDH) (Boehringer Yamanouchi) (300 units/ml) and L-lactate dehydrogenase (L-LDH) (Sigma Chemical Co.) (900 units/ml) in 100 mM sodium phosphate buffer (pH 7.0) and the mixture is allowed to stand at 0° C. to 4° C. for 1 day for enzyme immobilization. The thus-obtained immobilized enzyme-bearing carrier support is packed into an acrylic resin column (3.5 mm in inside diameter, 30 mm in length) to give a column containing immobilized D-LDH and L-LDH.

(4) Assay apparatus (I)

Figure 4:
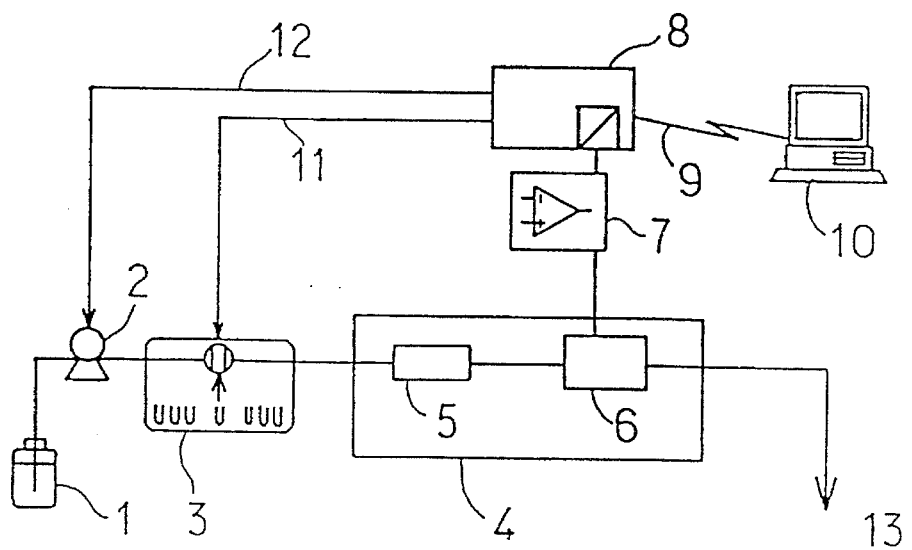
FIG. 4 shows another embodiment of the invention.

L-lactic acid assay is performed using a flow-type assay apparatus as shown in FIG. 4. A buffer solution is fed from a buffer tank (1) by means of a pump (2) while 5 μl of a sample is injected into the assay apparatus via a sampler (3). The sample injected passes through the aforementioned immobilized LOD column (5) in a constant-temperature vessel (4) maintained at 30° C., whereupon hydrogen peroxide is formed from L-lactic acid. The change in electric current is detected by a hydrogen peroxide electrode (6). The change in electric current at the electrode is detected by a detector (7). The signals may be transmitted to a personal computer (10). The hydrogen peroxide electrode (6) comprising a working electrode, a reference electrode and a counter electrode is housed in a cell and incorporated into the L-lactic acid assay apparatus.

In FIG. 4, (8), (9), (11), (12) and (13) represent a single board computer, RS232C code, sampler controling signal, pump controling signal and discharge, respectively.

The buffer solution has a pH of 7.0 and the following composition: 100 mM sodium phosphate, 50 mM potassium chloride and 1 mM sodium azide. The rate of flow through the pump is 1.0 ml/minute.

(5) Assay apparatus (II)

L-Lactic acid and D-lactic acid are assayed using a flow-type assay apparatus as shown in FIG. 1. A buffer solution is fed from a buffer tank (1') by means of a pump (2') while 1 μl of a sample is injected into the apparatus via a sampler (3'). The sample injected is divided into two streams by a three-way joint (5'). One passes through an L-lactate oxidase column (6'), where upon hydrogen peroxide is formed from L-lactic acid and the change in electric current is detected by a hydrogen peroxide electrode (7'). This electrode is referred to as first electrode. The other passes through a D-LDH/L-LDH column (8'), whereupon conversion of D-lactic acid and L-lactic acid takes place. The conversion mixture passes through another L-lactate oxidase column (9') and the change in electric current is detected by another hydrogen peroxide electrode (10'). This electrode is referred to as second electrode. The columns and electrodes are disposed in a constant-temperature vessel (4') maintained at 30° C. The change in electric current at each electrode is detected by a detector (11'). The signals may be transmitted to a personal computer (14').

In FIG. 1, (12'), (13'), (15'), (16') and (17') represent a single board computer, RS232C code, sampler controling signal, pump controling signal and discharge, respectively.

The composition of the buffer, which has a pH of 7.0, is as follows: 100 mM sodium phosphate, 50 mM potassium chloride, 1 mM sodium azide and 5 mM NAD. The rate of flow through the pump is 1.3 ml/minute, the flow rate at the first electrode is 0.7 ml/minute, and the flow rate at the second electrode is 0.6 ml/minute.

Example 2

Using an assay apparatus I (FIG. 4), electrode (6) and columns as prepared in Example 1 (1) and (2), the following assay was conducted.

Standard sample solutions containing 5 mM NAD, having a pH of 7.0 and differing in lactic acid content as shown below were prepared with and without adding the enzymes as follows: D-LDH 54.3 units/ml and L-LDH 54.3 units/ml.

To each solutions with or without D- and L-LDH, D-lactic acid with concentrations of 1, 2, 5, 10 mM or L-lactic acid with concentrations of 1, 2, 5 10 mM were added to prepare standard solutions of D- and L-lactic acid. Distilled water with or without enzymes were used as a control sample. The solutions supplemented with the enzymes were incubated at 30° C. for more than 10 minutes (about 20 minutes) to equilibrate the solutions and then subjected to a lactic acid assay. The enzyme-free solutions were subjected to a lactic acid assay without incubation. As samples with or without L- and D-LDH, the following (a) to (c) were prepared:

(a) 2.5 mM D-Lactic acid+5 mM L-lactic acid;
(b) 5 mM D-lactic acid+2.5 mM L-lactic acid;
(c) 5 mM D-lactic acid+5 mM L-lactic acid.

The standard solutions were assayed for lactic acid to prepare working curves for L-lactic acid and D-lactic acid by using electric current values, respectively.

The results obtained are shown in Table 1.

TABLE 1

| Standard solution | Electric current (nA) | |
|---|---|---|
| | Without enzyme | After D- and L-isomer conversionf reaction |
| Control | 0 | 0 |
| 1 mM L-Lactic acid | 54 | 27 |
| 2 mM L-Lactic acid | 108 | 54 |
| 5 mM L-Lactic acid | 271 | 138 |
| 10 mM L-Lactic acid | 557 | 274 |

TABLE 1-continued

| Standard solution | Electric current (nA) | |
|---|---|---|
| | Without enzyme | After D- and L-isomer conversionf reaction |
| 1 mM D-Lactic acid | 0 | 27 |
| 2 mM D-Lactic acid | 0 | 53 |
| 5 mM D-Lactic acid | 0 | 139 |
| 10 mM D-Lactic acid | 0 | 273 |

The current values shown in Table 1 as obtained for the standard lactic acid solutions without enzyme addition and the incubated standard lactic acid solutions supplemented with the enzymes gave the following three working curves.

*Working curve 1 (without enzyme addition)

Working curve for L-lactic acid:

$Y = 55.66\ X - 2.44$

*Working curve 2 (with enzyme addition)

Working curve for L-lactic acid $Y = 27.54\ X - 0.52$

*Working curve 3 (with enzyme addition)

Working curve for D-lactic acid $Y = 27.36\ X - 0.39$

In the above working curves, Y stands for the current value (nA) and X for the lactic acid concentration (mM) in the sample before incubation.

Then, the above-mentioned three samples supplemented with the enzymes were incubated at 30° C. for about 20 minutes to equilibrate the samples and, together with the three corresponding enzyme-free samples, assayed for L-lactic acid and D-lactic acid concentrations using the above working curves.

The results thus obtained are shown in Table 2.

TABLE 2

| Sample (mM) | | Electric current (nA) | | Assayed value (mM) | |
|---|---|---|---|---|---|
| D-lactic acid | L-lactic acid | Without enzyme | After isomer conversion reaction | D-lactic acid | L-lactic acid |
| 2.5 | 5.0 | 272 | 203 | 2.45 | 4.93 |
| 5.0 | 2.5 | 136 | 202 | 4.86 | 2.49 |
| 5.0 | 5.0 | 273 | 275 | 5.02 | 4.95 |

Example 3

Five commercial lactic acid drinks, A (Kansai Luna's yoghurt), B (Yakult's fermented milk), C (Kyodo Nyugyo's sterilized lactic acid bacteria beverage), D (Snow Brand Milk Product's yoghurt) and E (Snow Brand Milk Product's fermented milk), were assayed for D-lactic acid, L-lactic acid and total lactic acid. Thus, each sample was diluted 20- to 40-fold, then contacted with NAD, D-LDH and L-LDH in solution and, after a certain period, subjected to L-lactic acid concentration determination.

The L-lactic acid concentration determination was conducted in the same manner as Exmple 2 by immobilizing L-lactate oxidase and quantitating the product hydrogen peroxide using a hydrogen peroxide electrode (FIG. 4). The immoblized L-lactate oxidase-containing column (5), the hydrogen peroxide electrode (6) with a platinum electrode as the working electrode, and the L-lactic acid assay apparatus used were the same as those used in Example 2 (FIG. 4).

(1) Assay method

1) For L-lactic acid assay, the diluted samples were used as such and the L-lactic acid concentrations were determined.

2) L-Lactic acid assay after enzymatic isomer conversion reaction in a buffer solution: To 0.5 ml of each diluted sample was added 0.5 ml of a reaction medium containing 10 mM NAD, 10 units/ml D-LDH, 50 units/ml L-LDH and 200 mM phosphate (pH 7.5). The mixture was allowed to stand at room temperature for at least 2 hours to thereby allow the reaction to proceed and, after the conversion reaction, the L-lactic acid concentration was determined. A working curve was constructed by assaying 1, 2 and 5 mM L-lactic acid and distilled water as a control sample. The lactic acid concentrations (%) in the original samples were calculated from the measured values obtained.

(2) Results

The D-lactic acid, L-lactic acid and total lactic acid concentrations (%) in the five lactic acid drinks were as shown in Table 3.

TABLE 3

| | COMPARATIVE EXAMPLE 1 | | |
| --- | --- | --- | --- |
| Sample | D-Lactic acid % | L-Lactic acid % | Total Lactic acid % |
| A | 1.14 | 0.25 | 1.40 |
| B | 0.01 | 0.78 | 0.80 |
| C | 0.11 | 0.24 | 0.35 |
| D | 0.53 | 0.60 | 1.13 |
| E | 0.55 | 0.34 | 0.90 |

The above five commercially available lactic acid drinks A to E were assayed for D-lactic acid, L-lactic acid and total lactic acid concentrations using F Kit (Boehringer Yamanouchi).

(1) Assay method

In this comparative example, the sample dilutions were centrifuged (18,000 rpm, 20 minutes) for removing the precipitate fraction to thereby eliminate the influence of sample turbidity and thus enabling exact absorbance measurement in the ultraviolet region (340 nm). Thus, a pretreatment step was required. The lactic acid concentrations in each dilution were determined based on the absorbance values obtained and then converted by calculation to the lactic acid concentrations (%) in the corresponding original sample.

Thus, using F Kit, NAD, glutamic acid, glutamic-pyruvic transaminase were admixed with each assay sample and the absorbance at 340 nm was measured using a spectrophotometer and used as a control sample.

Then, D-LDH was further added and the mixture was allowed to stand for 20 minutes and then subjected to absorptiometry. The D-lactic acid in each sample was calculated based on the change in absorbance as caused by D-LDH.

For assaying L-lactic acid, L-LDH was added to the above reaction mixture and, after mixing, the mixture was allowed to stand for 20 minutes, followed by absorbance measurement. The L-lactic acid concentration in each sample was calculated from the change in absorbance as caused by L-LDH.

(2) Results

The D-lactic acid, L-lactic acid and total lactic acid concentrations (%) in the five lactic acid drinks were as shown in Table 4.

TABLE 4

| Sample | D-Lactic acid % | L-Lactic acid % | Total Lactic acid % |
| --- | --- | --- | --- |
| A | 1.13 | 0.22 | 1.35 |
| B | 0.01 | 0.77 | 0.78 |
| C | 0.11 | 0.24 | 0.35 |
| D | 0.52 | 0.61 | 1.13 |
| E | 0.54 | 0.32 | 0.86 |

Based on these values, the correlationships between the assay values (Y) obtained in Example 3 by the method of this invention and those (X) obtained in Comparative Example 1 using F Kit were examined.

D-Lactic acid assay values $Y = 1.02 X + 0.00$ ($r = 1.000$);

L-Lactic acid assay values $Y = 0.98 X + 0.02$ ($r = 0.998$);

Total lactic acid assay values $Y = 1.03 X - 0.01$ ($r = 0.999$).

Good agreement was revealed for each of D-lactic acid, L-lactic acid and total lactic acid, indicting that exact and precise assays are possible by the method of the invention. The assay method of the invention was not influenced by sample turbidity, hence the pretreatment mentioned above could be omitted.

The assay method of the invention is more accurate and easier to to operate than the F kit method, because of the fewer number of using pipette. Further, the range of concentration of optical isomers are wider.

Example 4

(1) Assaying of standard solutions

Distilled water, 1, 2, 5 and 10 mM L-lactic acid and 2, 5, 10, 20 and 50 mM D-lactic acid were respectively injected into the assay apparatus (II) mentioned in Example 1 (5) (FIG. 1). The current values obtained via the first and second electrodes were as shown in Table 9, and the working curves shown below were obtained, wherein Y is the current value (nA) and X is the lactic acid concentration (mM) in the sample.

Since the first electrode (7') reacts only with L-lactic acid, so that working curve 1 is exclusively for L-lactic acid. At the second electrode (10'), the L-lactic acid/D-lactic acid conversion reaction takes place and, in assaying standard L-lactic acid solutions, L-lactic acid decreases at a certain constant rate and, in assaying standard D-lactic acid solutions, D-lactic acid is converted to L-lactic acid at a certain constant rate and the latter is detected. Since either of D-lactic acid and L-lactic acid can thus be detected, working curve 2 for L-lactic acid and working curve 3 for D-lactic acid can be obtained.

Working curve 1 (for L-lactic acid), first electrode $Y = 15.5 X + 0.9$

Working curve 2 (for L-lactic acid), second electrode $Y=11.8\ X-0.6$

Working curve 3 (for D-lactic acid), second electrode $Y=1.5\ X-0.6$

TABLE 5

| Standard solution | Electric current (nA) | |
|---|---|---|
| | First electrode | Second electrode |
| Control | 0 | 0 |
| 1 mM L-Lactic acid | 16 | 11 |
| 2 mM L-Lactic acid | 33 | 23 |
| 5 mM L-Lactic acid | 79 | 58 |
| 10 mM L-Lactic acid | 155 | 118 |
| 2 mM D-Lactic acid | 0 | 2 |
| 5 mM D-Lactic acid | 0 | 7 |
| 10 mM D-Lactic acid | 0 | 14 |
| 20 mM D-Lactic acid | 0 | 29 |
| 50 mM D-Lactic acid | 0 | 74 |

(2) Assaying of mixture samples

Mixtures of D-lactic acid and L-lactic acid were injected into the assay apparatus (II) mentioned in Example 1 (5) (FIG. 1). The current values obtained via the first and second electrodes and the D-lactic acid and L-lactic acid concentrations as calculated using the working curves obtained by assaying the standard solutions were as shown in Table 6. For calculating the lactic acid concentrations in an unknown sample, the L-lactic acid concentration in the sample is first determined by applying the current value obtained via the first electrode (7') to working curve 1. Based on said concentration, the current value for L-lactic acid involved in the reaction at the second electrode is determined using working curve 2. Subtraction of said current value for L-lactic acid from the current value obtained at the second electrode (10') gives the current value produced by D-lactic acid. By applying this value to working curve 3, the D-lactic acid concentration can be determined.

TABLE 6

| Sample (mM) | | Electric current (nA) | | Assayed value (mM) | |
|---|---|---|---|---|---|
| L-lactic acid | D-lactic acid | first electrode | second electrode | L-lactic acid | D-lactic acid |
| 1 | 5 | 16 | 18 | 1.0 | 5.2 |
| 1 | 25 | 16 | 48 | 1.0 | 25.2 |
| 1 | 50 | 15 | 85 | 0.9 | 50.3 |
| 2.5 | 5 | 39 | 35 | 2.5 | 4.8 |
| 5 | 5 | 78 | 65 | 5.0 | 5.0 |

The lactic acid assay method of the invention makes it possible to assay D-lactic acid and L-lactic acid exactly and precisely in a simple and easy manner.

The method of the invention has the following features, among others. The number of pipetting operations is smaller and the procedure is easier as compared with the F Kit method. The number of reagents and enzymes required is also small and this facilitates the procedure and reduces the cost of analysis. The assayable concentration range is wide and can be varied by varying the sample size to be injected into the assay apparatus. When a sample injector is used in assaying, man power saving is possible.

By using the assay apparatus of the invention, it is now possible to assay D-lactic acid and L-lactic acid exactly and precisely in a simple manner within a short period of time. According to an embodiment shown in Example 4 of the invention, repeated use of the enzymes L-LDH and D-LDH in immobilized form is possible and the enzymatic reaction conditions can be readily adjusted, even in a case that conversion reaction time is short, in contrast with the procedures for assaying D-lactic acid and L-lactic acid using L-LDH and L-LDH in solution form.

Example 5

(1) Production of a column containing immobilized L-lactate oxidase

An immobilized L-lactate oxidase-containing column was prepared in the same manner as in Example 1.

(2) Production of a column containing immobilized D-LDH and L-LDH

A column containing immobilized D-LDH and L-LDH was prepared in the same manner as in Example 1.

(3) Production of a hydrogen peroxide electrode

A hydrogen peroxide electrode was prepared in the same manner as in Example 1.

(4) Assay apparatus

Figure 5:
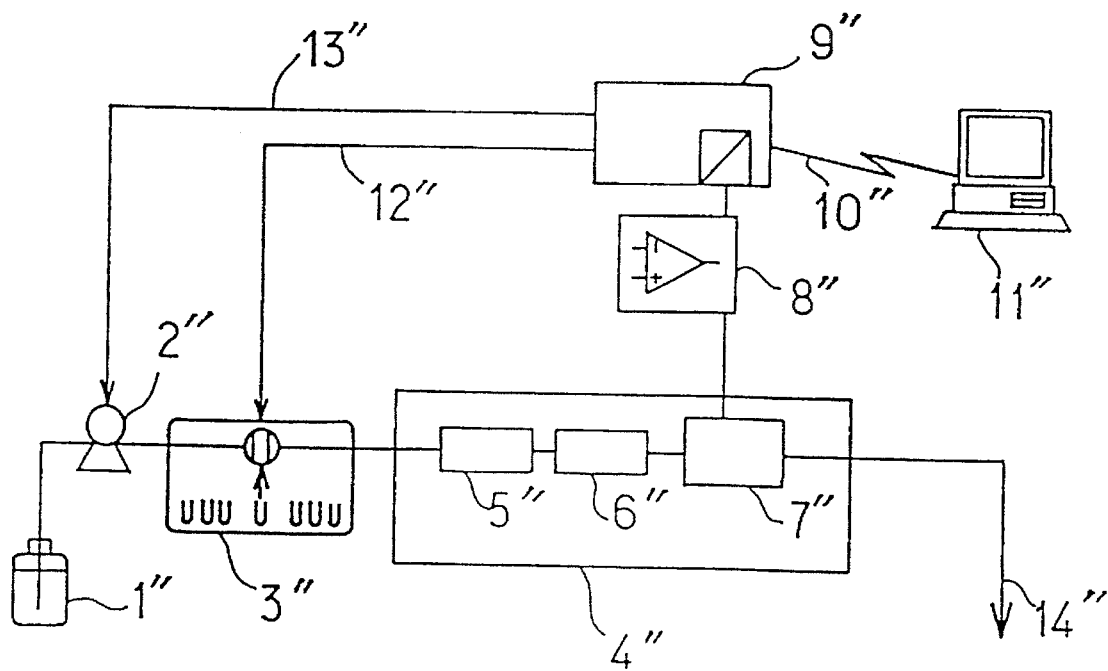
FIG. 5 shows an apparatus used in this invention.

L-Lactic acid and D-lactic acid are assayed using the flow-type assay apparatus shown in FIG. 5. A buffer solution is fed from a buffer tank (1") by means of a pump (2") while 1 μl of a sample is injected into the assay apparatus via a sampler (3"). The sample injected passes through an immobilized D-LDH and L-LDH column (5"), where a converting reaction of D-lactic acid and L-lactic acid is occurred when NAD is added. Subsequently, the sample passes through a L-LOD-immobilized column (6") and the change in electric current value is detected by means of a hydrogen peroxide electrode (7"). These columns and electrode are placed in a constant-temperature vessel (4") maintained at 30° C. The change in electric current at the electrode is detected by a detector (8"). The signals may be transmitted to a personal computer (11").

In FIG. 5, (9"), (10"), (12"), (13") and (14") represent a single board computer, RS232C code, sampler controlling signal, pump controlling signal and discharge, respectively.

The buffer solution has a pH of 7.0 and the following composition: 100 mM sodium phosphate, 50 mM potassium chloride and 1 mM sodium azide. To the buffer solution, 5 mM of NAD is added when isomer conversion reaction is needed. The rate of flow through the pump is 0.6 ml/minute.

(5) Assaying of standard solutions

Distilled water, 1, 2 and 5 mM L-lactic acid and 2, 5 and 10 mM D-lactic acid were respectively injected into the assay apparatus mentioned in (4) (FIG. 5) and assayed. For each sample, assaying was performed with and without 5 mM NAD in each buffer solution. When NAD is added, an isomer conversion reaction is occurred. The electric current values detected were as shown in Table 11, giving the following working curves, wherein Y is the electric current value (nA) and X is the lactic acid concentration (mM) in the sample.

Working curve 1 (for L-lactic acid), without NAD $Y=27.74\ X+0.204$

Working curve 2 (for L-lactic acid), with NAD $Y=22.04\ X+0.064$

Working curve 3 (for D-lactic acid), with NAD $Y=6.13\ X+0.004$

TABLE 7

| Standard solution | Electric current value (nA) | |
|---|---|---|
| | Without NAD | With NAD |
| blank | 0 | 0 |
| 1 mM L-lactic acid | 28 | 22 |
| 2 mM L-lactic acid | 56 | 44 |
| 5 mM L-lactic acid | 139 | 110 |
| 2 mM D-lactic acid | 0 | 12 |
| 5 mM D-lactic acid | 0 | 31 |
| 10 mM D-lactic acid | 0 | 61 |

(6) Assaying of mixture samples

Mixtures of D-lactic acid and L-lactic acid were respectively assayed with and without addition of NAD using the assay apparatus mentioned in (4) (FIG. 5). The electric current values obtained and the D-lactic acid and L-lactic acid concentrations calculated using the working curves obtained by assaying the standard solutions were as shown in Table 8. The lactic acid concentrations in unknown samples were calculated in the same manner as in Example 4.

TABLE 8

| Sample (mM) | | Electric current (nA) | | Assayed value (mM) | |
|---|---|---|---|---|---|
| L-lactic acid | D-lactic acid | first electrode | second electrode | L-lactic acid | D-lactic acid |
| 2 | 2 | 56 | 56 | 2.0 | 2.0 |
| 2 | 5 | 56 | 75 | 2.0 | 5.0 |
| 5 | 2 | 139 | 123 | 5.0 | 2.0 |

Example 6

As an example of aspect II of the invention, the following assay was conducted by using apparatus (I) (FIG. 4), a column and an electrode prepared in Example 1 (1), (2) and (4).

(1) Assay of L-lactic acid and D-lactic acid

L-Lactic acid, D-lactic acid and L-lactic acid/D-lactic acid mixtures were assayed in two processes, namely (1) in the form of samples as such and (2) in the form of reaction mixtures after treatment with D-LDH, L-LDH and NAD for attaining a 1:1 equilibrium between D-lactic acid and L-lactic acid. For obtaining appropriate racemization conditions, 0.2 ml of a reagent solution having a pH of 7.5 and containing 50 units/ml L-LDH, 20 units/ml D-LDH, 10 mM NAD and 200 mM sodium phosphate was added to 0.2 ml of each sample, and the mixture was allowed to stand at room temperature for 60 minutes. The sample or standard solutions were injected in 5-µl portions and electric current values were obtained. The standard solutions used were 1, 2 and 5 mM L-lactic acid, and distilled water as a control sample. A working curve was obtained from the data obtained with the standard solutions. And the current values for the samples were converted by calculation to L-lactic acid concentrations (mM).

The working curve obtained is shown, in terms of an equation, as working curve A, wherein X is the lactic acid concentration in the sample and Y is the current value. The results are summarized in Table 9.

Working curve A (working curve for L-lactic acid)

$Y = 44.87 X + 0.59$.

TABLE 9

| Sample (mM) | | Electric current (nA) | | L-Lactic acid assay value (mM) | | D-Lactic acid assay value (mM) |
|---|---|---|---|---|---|---|
| L-Lactic acid | D-Lactic acid | (1) | (2) After reaction | (1) | (2) After reaction | |
| 5.00 | 0.00 | 225 | 57 | 5.00 | 1.25 | 0.00 |
| 0.00 | 5.00 | 0 | 56 | 0.00 | 1.24 | 4.94 |
| 2.50 | 2.50 | 112 | 57 | 2.49 | 1.25 | 2.51 |
| 5.00 | 5.00 | 224 | 112 | 4.99 | 2.49 | 4.98 |

In Table 9, the data shown in columns (1) are the results of L-lactic acid assay as expressed in terms of current value and L-lactic acid concentration. The data in columns (2) are the current values as produced by L-lactic acid after the racemization reaction and the corresponding L-lactic acid assay values. The D-lactic acid concentrations were calculated by doubling the L-lactic acid concentration in each reaction mixture (because each sample was diluted to ½), further doubling the resulting product (because of the L-lactic acid content after racemization being ½ of the total lactic acid content) to obtain the total lactic acid content, and subtracting the L-lactic acid content in the original sample from said total lactic acid content.

(2) Assay of L-lactic acid and pyruvic acid

L-Lactic acid, pyruvic acid and mixtures of L-lactic acid and pyruvic acid sample were assayed in two processes, namely (1) in the form of samples as such and (2) after conversion of pyruvic acid to L-lactic acid by treatment with L-LDH and NADH in a solution. The reaction conditions were as follows: 0.2 ml of a reagent solution having a pH of 7.0 containing 2 units/ml L-LDH, 10 mM NADH and 200 mM sodium phosphate was added to 0.2 ml of each sample and the mixture was allowed to stand at room temperature for 30 minutes. The samples or standard solutions were injected in 5-µl portions and electric current values were obtained. Used as the standard solutions were 1, 2 and 5 mM L-lactic acid, and distilled water as a control sample. A working curve was obtained using the standard solutions, and the current data for the samples were converted by calculation to L-lactate concentrations (mM).

The working curve obtained is shown below, in terms of an equation, as working curve B. The results are summarized in Table 10.

Working curve B (working curve for L-lactic acid)

$Y = 41.21 X + 0.53$.

TABLE 10

| Sample (mM) | | Electric current (nA) | | L-Lactic acid assay value (mM) | | Pyruvic acid assay value (mM) |
|---|---|---|---|---|---|---|
| L-Lactic acid | Pyruvic acid | (1) | (2) After reaction | (1) | (2) After reaction | |
| 2.50 | 2.08 | 104 | 95 | 2.50 | 2.30 | 2.09 |
| 1.00 | 2.08 | 41 | 64 | 0.99 | 1.54 | 2.09 |
| 0.00 | 2.08 | 0 | 43 | 0.00 | 1.04 | 2.07 |
| 2.50 | 0.00 | 103 | 52 | 2.49 | 1.25 | 0.00 |
| 2.50 | 0.42 | 103 | 61 | 2.49 | 2.91 | 0.43 |

In Table 10, the data shown in columns (1) are the current values and L-lactic acid assay values as obtained by assaying the samples for L-lactic acid, and the data shown in columns (2) are the L-lactic acid assay values obtained after conversion of pyruvic acid to L-lactic acid. For obtaining the pyruvic acid concentrations, the L-lactic acid concentrations after reaction were doubled (because each sample to diluted to ½) and the L-lactic acid assay values for the corresponding samples are subtracted from the doubled results. In the working curve, Y stands for the current value (nA) and X for the lactic acid concentration (mM) in the sample.

Example 7

(1) Method of producing a column containing immobilized LOD

An immobilized LOD-containing column was prepared in the same manner as in Example 1.

(2) Method of producing a hydrogen peroxide electrode

A hydrogen peroxide electrode was prepared in the same manner as in Example 1.

(3) Assay apparatus (I)

The same L-lactic acid assay apparatus as used in Example 1 (4) (FIG. 4) was used.

(4) Assaying of actual samples

Seven commercially available lactic acid drinks were each subjected to the same assay procedure as in Example 6 after 20- to 40-fold dilution. L-Lactic acid assaying was conducted (1) diluted sample as such, (2) after addition of 0.2 ml of a reagent solution having a pH of 7.5 and containing 50 units/ml L-LDH, 20 units/ml D-LDH, 10 mM NAD and 200 mM sodium phosphate to 0.2 ml of each dilution, followed by 60 minutes of incubation at room temperature, and (3) after addition of 0.2 ml of a reagent solution having a pH of 7.0 and containing 2 units/ml L-LDH, 10 mM NADH and 200 mM sodium phosphate to 0.2 ml of each diluted sample, followed by 30 minutes of incubation at room temperature. The sample and standard solutions were injected in 5-μl portions, and electric current values were obtained. 1, 2 and 5 mM L-lactic acid were used as the standard solutions, and distilled water as a control sample. A working curve was obtained based on data for the standard solutions, and the current values for the samples were converted by calculation to L-lactic acid concentrations (mM). The thus-obtained L-lactic acid, D-lactic acid and pyruvic acid concentrations (%) in the samples are shown in Table 15.

TABLE 11

| Sample | Concentration in sample (%) | | |
|---|---|---|---|
| | L-Lactic acid | D-Lactic acid | Pyruvic acid |
| A | 0.63 | 0.04 | 0.00 |
| B | 1.04 | 0.00 | 0.00 |
| C | 0.78 | 0.01 | 0.01 |
| D | 0.27 | 0.01 | 0.00 |
| E | 0.64 | 0.50 | 0.01 |
| F | 0.25 | 1.14 | 0.00 |
| G | 0.74 | 0.35 | 0.01 |

| Sample | Sort | Manufacturer | Trademark |
|---|---|---|---|
| A | Lactic acid drink | Yakult | Yakult |
| B | Fermented milk | Yakult | Joie Plain |
| C | Fermented milk | Yakult | Joie Mandarin |
| D | Lactic acid drink | Sunlite | MySour |
| E | Yoghurt | Snow Brand Milk Product | Yogur |
| F | Fermented milk | Kansai Luna | Nomu Yoghurt |
| G | Yoghurt | Meiji Milk Product | Bulgaria Yoghurt |

Furthermore, each sample was centrifuged (20,000 rpm, 20 minutes) and then subjected to assaying using the D/L-lactic acid assay system of F Kit. As shown below in terms of correlationship, the data thus obtained were in good agreement with the data obtained above by the method of the invention.

The assay procedure using F Kit (Boehringer Yamanouchi) was as follows.

NAD, glutamic acid and glutamic-pyruvic transaminase were added to each sample and, after mixing, the absorbance at 340 nm was measured using a spectrophotometer. This data was used as a control. Further, D-LDH was admixed with the above mixture and, after 20 minutes of standing, absorbance measurement was performed in the same manner. The D-lactic acid concentration in the sample was calculated from the change in absorbance as caused by D-LDH.

For assaying L-lactic acid, L-LDH was admixed with the above mixture and, after 20 minutes of standing, absorbance measurement was carried out. The L-lactic acid concentration in the sample was calculated from the change in absorbance as caused by L-LDH.

L-Lactic acid $Y=1.03\ X+0.01$ (correlation coefficient 0.999)

D-Lactic acid $Y=1.02\ X-0.00$ (correlation coefficient 1.000)

In the above equations, Y stands for the assay result obtained by the method of the invention and X for the assay result obtained with F Kit.

The method of the invention is not affected by turbidity or coloring matter, hence does not require such pretreatment as centrifugation. The number of reagents to be used is small and the number of pipetting operations is also small and, therefore, the procedure is simple. While, in assaying L-lactic acid and D-lactic acid by the F Kit method, the degree of dilution of samples to be subjected to assaying must be varied if the D:L ratios show wide differences, the method of the invention, by assaying L-lactic acid, can show the same level of sensitivity in total lactic acid determination, for instance, at a concentration four times higher and thus can give precise assay results in assaying unknown samples with a smaller number of repetitions.

We claim:

1. A method of assaying the L- and D-optical isomers in a sample which comprises:

(I)

(I-1) the step of assaying the L-optical isomer as occurring in said sample;

(I-2A) subjecting said sample to an enzymatic reaction in the presence of a L-dehydrogenase and a D-dehydrogenase of the isomers and a coenzyme, and converting the L-optical isomer in the sample to D-optical isomer and/or the D-optical isomer in the sample to L-optical isomer; and (I-2B) assaying the L-optical isomer after said enzymatic reaction;

or (II)

(II-1) the step of assaying the D-optical isomer as occurring in said sample;

(II-2A) subjecting said sample to an enzymatic reaction in the presence of a L-dehydrogenase and a D-dehydrogenase of the isomers and an oxidized coenzyme, and converting the L-optical isomer in the sample to D-optical isomer and/or the D-optical isomer in the sample to L-optical isomer; and (II-2B) assaying the D-optical isomer after said enzymatic reaction.

2. A method as defined in claim 1, wherein in (I) both steps of assaying the L-optical isomer (I-1) and (I-2B) comprise oxidizing the optical isomer using an oxidase for said L-optical isomer and detecting the change in the concentration of an electronically active substance as resulting from the reaction involving said oxidase;

and in (II) both steps of assaying the D-optical isomer (II-1) and (II-2B) comprise oxidizing the D-optical isomer using an oxidase for said D-optical isomer and detecting the change in the concentration of an electrochemically active substance as resulting from the reaction involving said oxidase.

3. A method as defined in claim 1, wherein, in steps (I-2A), (II-2A), said enzymatic reaction is performed in a reactor containing an immobilized L-dehydrogenase and an immobilized D-dehydrogenase.

4. A method as defined in claim 1, wherein in (I) said step of assaying the L-optical isomer in said sample comprises oxidizing the L-optical isomer using an oxidase for said L-optical isomer and detecting the change in the concentration of an electrochemically active substance as resulting from the reaction involving said oxidase;

and in (II) said step of assaying the D-optical isomer in said sample comprises oxidizing the D-optical isomer using an oxidase for said D-optical isomer and detecting the change in the concentration of an electrochemically active substance as resulting from the reaction involving said oxidase.

5. A method as defined in claim 1, wherein in (I) both steps of assaying the L-optical isomer in said sample comprises oxidizing the L-optical isomer using an oxidase for said L-optical isomer and detecting the change in the concentration of hydrogen peroxide produced or oxygen consumed which is an electrochemically active substance, as resulting from the reaction involving said oxidase by an amperometric method using electrode; and in (II) both steps of assaying the D-optical isomer in said sample comprises oxidizing the D-optical isomer using an oxidase for said D-optical isomer and detecting the change in the concentration of hydrogen peroxide produced or oxygen consumed which is an electrochemically active substance as resulting from the reaction involving said oxidase by an amperometric method using electrode.

6. A method as defined in claim 1, wherein in (I) said step (I-2A), said enzymatic reaction between L- and D-optical isomer is conducted in a solution containing L-dehydrogenase and D-dehydrogenase; and in (II) said step (II-2A), said enzymatic reaction between L- and D-optical isomer is conducted in a solution containing L-dehydrogenase and D-dehydrogenase.

7. A method as defined in claim 1, wherein said L-optical isomer and D-optical isomer are L-lactic acid and D-lactic acid, and said L-dehydrogenase and D-dehydrogenase are L-lactate dehydrogenase and D-lactate dehydrogenase, respectively.

8. An apparatus for assaying the L- and D-optical isomers in a sample by the flow technique which comprises:

(I)

(I-i) means for injecting the sample into a carrier being fed from upstream of a reactor;

(I-ii) a reactor containing said dehydrogenase for the D-optical isomer and a dehydrogenase for the L-optical isomer in immobilized form; and (I-iii) an immobilized oxidase for the L-optical isomer and an electrode for detecting the change in the concentration of an electrochemically active substance as resulting from the oxidation of the L-optical isomer in the sample by the action of the immobilized oxidase for said L-optical isomer and said immobilized oxidase being disposed downstream from said reactor; or (II)

(II-i) means for injecting the sample into a carrier being fed from upstream of a reactor; or (II-ii) a reactor containing said dehydrogenase for the D-optical isomer and a dehydrogenase for the L-optical isomer in immobilized form; and (II-iii) an immobilized oxidase for the D-optical isomer and an electrode for detecting the change in the concentration of an electrochemically active substance as resulting from the oxidation of the D-optical isomer in the sample by the action of the immobilized oxidase for said D-optical isomer and said immobilized oxidase being disposed downstream from said reactor.

9. An apparatus as defined in claim 8, which further comprises means for stopping the feeding of said carrier or reducing the rate of flow of said carrier such that the carrier containing the sample remains in contact with each of the dehydrogenase for the D-optical isomer and the dehydrogenase for the L-optical isomer in immobilized form.

10. An apparatus as defined in claim 8, which further comprises, in (I) upstream of said reactor, an immobilized oxidase for L-optical isomer and an electrode for detecting the change in the concentration of an electrochemically active substance as resulting from the oxidation of L-optical isomer in the sample by the action of the immobilized oxidase for the L-optical isomer; and in (II) upstream of said reactor, an immobilized oxidase for D-optical isomer and an electrode for detecting the change in the concentration of an electrochemically active substance as resulting from the oxidation of D-optical isomer in the sample by the action of the immobilized oxidase for the D-optical isomer.

11. An apparatus as defined in claim 8, wherein the L- and D-optical isomers are L-lactic acid and D-lactic acid, respectively.

12. A method of assaying the D- and L-optical isomers in a sample which comprises performing two assays by using the apparatus as defined in claim 8, one in the presence of an oxidized coenzyme and the other in the absence of an oxidized coenzyme, by contacting the sample with a D-dehydrogenase and a L-dehydrogenase each in an immobilized form.

13. An apparatus as defined in claim 8, wherein the D-form dehydrogenase and L-form dehydrogenase are immobilized by reacting a support having hydroxyl groups with an aminosilane reagent to convert the hydroxyl groups to aminosilane groups, reacting the amino group portions of the aminosilane groups formed on the surface of the support with a polyfunctional aldehyde to bond the polyfunctional aldehyde thereto, and bonding D-form dehydrogenase and L-form dehydrogenase to the polyfunctional aldehyde.

14. In a method of assaying the D- and L-optical isomers in a sample wherein the method comprises the steps of:

(I)

(I-1) contacting the sample and an oxidized coenzyme with an enzyme system containing a D-dehydrogenase and a L-dehydrogenase to convert the D-optical isomer in the sample to L-optical isomer and/or the L-optical isomer in said sample to D-optical isomer and (I-2) detecting electrochemically the change in the concentration of an electrochemically active substance as resulting from the oxidation of the L-optical isomer in the sample by the action of an oxidase for the L-optical isomer, and (I-a) in step (I-2), obtaining a first working curve showing the relation between the concentration of the L-optical isomer and the output value in electrochemical detection using standard solutions of the L-optical isomer as samples, (I-b) performing step (I-1) using standard solutions of the L-optical isomer as samples and subsequently performing step (I-2) to obtain a second working curve showing the relation between the concentration of the L-optical isomer and the output value in electrochemical detection, (I-c) performing step (I-1) using standard solutions of the D-optical isomer as samples and subsequently performing step (I-2) to obtain a third working curve showing the relation between the concentration of the D-optical isomer and the output value in electrochemical detection, (I-d) further performing step (I-2) using the assay sample to obtain a first output value, (I-e) performing step (I-1) suing the assay sample and subsequently performing step (I-2) to obtain a second output value, and calculating the content of the D- and L-optical isomers in the assay sample based on the first and second output values and the first, second and third working curves; or (II)

(II-1) contacting the sample and an oxidized coenzyme with an enzyme system containing a D-dehydrogenase and a L-dehydrogenase to convert the D-optical isomer in the sample to L-optical isomer and/or the L-optical isomer in said sample to D-optical isomer and (II-2) detecting electrochemically the change in the concentration of an electrochemically active substance as resulting from the oxidation of the D-optical isomer in the sample by the action of an oxidase for the D-optical isomer, and (II-a) in step (II-2), obtaining a first working curve showing the relation between the concentration of the D-optical isomer and the output value in electrochemical detection using standard solutions of the D-optical isomer as samples, (II-b) performing step (II-1) using standard solutions of the D-optical isomer as samples and subsequently performing step (II-2) to obtain a second working curve showing the relation between the concentration of the D-optical isomer and the output value in electrochemical detection, (II-c) performing step (II-1) using standard solutions of the D-optical isomer as samples and subsequently performing step (II-2) to obtain a third working curve showing the relation between the concentration of the D-optical isomer and the output value in electrochemical detection, (II-d) further performing step (II-2) using the assay sample to obtain a first output value, (II-e) performing step (II-1) using the assay sample and subsequently performing step (II-2) to obtain a second output value, and calculating the content of the D- and L-optical isomers in the assay sample based on the first and second output values and the first, second and third working curves.

15. A method as defined in claim 14, wherein the D-dehydrogenase and L-dehydrogenase are both immobilized on a support and packed in a reactor and wherein the carrier feeding is stopped or the rate of carrier flow is reduced such that the oxidized coenzyme and the sample remain in contact with the immobilized dehydrogenases.

16. A method as defined in claim 14, wherein (I) two parallel paths each comprising the oxidase for L-optical isomer, which is in an immobilized form, and an electrode are used and wherein in one of the paths, the L-optical isomer originally occurring in the sample is assayed using the immobilized oxidase for L-optical isomer and, in the other path, an immobilized enzyme containing the D-dehydrogenase and L-dehydrogenases is disposed in a position upstream of the immobilized oxidase for L-optical isomer and assaying the L-optical isomer after conversion of the D-optical isomer and L-optical isomer as caused by the D-dehydrogenase and L-dehydrogenase;

and in (II) two parallel paths each comprising the oxidase for D-optical isomer, which is in an immobilized form, and an electrode are used and wherein, in one of the paths, the D-optical isomer originally occurring in the sample is assayed using the immobilized oxidase for D-optical isomer and, in the other path, an immobilized enzyme containing the D-dehydrogenase and L-dehydrogenase is disposed in a position upstream of the immobilized oxidase for D-optical isomer and assaying the D-optical isomer after conversion of the D-optical isomer and L-optical isomer as caused by the D-dehydrogenase and L-dehydrogenase.

17. A method of assaying 3 components of the L-optical isomer, D-optical isomer and the oxidation product derived from the L-optical isomer or D-optical isomer as occurring in a sample which comprises the steps of:

(I)

(I-1) assaying the L-optical isomer in said sample, (I-2) subjecting the sample to an enzymatic reaction in the presence of a L-dehydrogenase and a D-dehydrogenase of said optical isomers and an oxidized coenzyme and converting the L-optical isomers in the sample to D-optical isomer and/or the D-optical isomer in the sample to L-optical isomer and subsequently assaying the L-optical isomer after said enzymatic reaction, and (I-3) contacting the sample with a L-dehydrogenase in the presence of a reduced coenzyme to convert an oxidation product in the sample to the L-optical isomer and assaying the L-optical isomer and calculating the concentration of L-optical isomer and D-optical isomer from the results of steps (I-1), (I-2), and calculating the concentration of the oxidation product derived from the L-optical isomer or D-optical isomer from the results of steps (I-1), (I-3); or (II)

(II-1) assaying the D-optical isomer in said sample, (II-2) subjecting the sample to an enzymatic reaction in the presence of a L-dehydrogenase and a D-dehydrogenase of said optical isomers and an oxidized coenzyme and converting the L-optical isomer in the sample to D-optical isomer and/or the D-optical isomer in the sample to L-optical isomer and subsequently assaying the D-optical isomer after said enzymatic reaction, and (II-3) contacting the sample with a D-dehydrogenase in the presence of a reduced coenzyme to convert an oxidation product in the sample to the D-optical isomer and assaying the D-optical isomer and calculating the concentration of L-optical isomer and D-optical isomer from the results of steps (II-1), (II-2), and calculating the concentration of the oxidation product derived from the L-optical isomer or the D-optical isomer from the results of steps (II-1), (II-3).

18. A method as defined in claim 17 where in (I) the step of assaying the L-optical isomer comprises oxidizing the L-optical isomer using an oxidase for the L-optical isomer and detecting the change in the concentration of an electrochemically active substance as resulting from the reaction involving said oxidase; and in (II) the step of assaying the D-optical isomer comprises oxidizing the D-optical isomer using an oxidase for the D-optical isomer and detecting the change in the concentration of an electrochemically active substance as resulting from the reaction involving said oxidase.

19. A method as defined in claim 18, wherein said electrochemically active substance is hydrogen peroxide the concentration of which increases upon the oxidase-involving reaction, or oxygen the concentration of which decreases upon said reaction.

20. A kit comprising:

(I-1) a first container containing a reagent comprising L-dehydrogenase and D-dehydrogenase of optical isomers and an oxidized coenzyme to convert L-optical isomer in a sample to D-optical isomer and/or D-optical isomer in a sample to L-optical isomer, or (I-2) a second container containing a reagent comprising L-dehydrogenase of the optical isomers and a reduced coenzyme to convert an oxidized-form of the optical isomer in a sample to L-optical isomer; or (II)

(II-1) a first container containing a reagent comprising L-dehydrogenase and D-dehydrogenase of optical isomers and an oxidized coenzyme to convert L-optical isomer in a sample to D-optical isomer and/or D-optical isomer in a sample to L-optical isomer, or (II-2) a second container containing a reagent comprising D-dehydrogenase of the optical isomers and a reduced coenzyme to convert an oxidized-form of the optical isomer in a sample into D-optical isomer.

\* \* \* \* \*